United States Patent
Schumacher et al.

(10) Patent No.: US 7,153,871 B2
(45) Date of Patent: Dec. 26, 2006

(54) PHOSPHODIESTERASE 4 INHIBITORS, INCLUDING AMINOINDAZOLE AND AMINOBENZOFURAN ANALOGS

(75) Inventors: Richard A. Schumacher, Monroe, NY (US); Allen T. Hopper, Glen Rock, NJ (US); Ashok Tehim, Ridgewood, NJ (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 292 days.

(21) Appl. No.: 10/622,117

(22) Filed: Jul. 18, 2003

(65) Prior Publication Data
US 2004/0087584 A1  May 6, 2004

Related U.S. Application Data

(60) Provisional application No. 60/396,726, filed on Jul. 19, 2002, provisional application No. 60/306,140, filed on Jul. 14, 2001, provisional application No. 60/267,196, filed on Feb. 8, 2001, provisional application No. 60/262,651, filed on Jan. 22, 2001.

(51) Int. Cl.
| C07D 405/12 | (2006.01) |
| C07D 405/14 | (2006.01) |
| A61K 31/443 | (2006.01) |
| A61K 31/4439 | (2006.01) |
| C07D 401/12 | (2006.01) |

(52) U.S. Cl. .................. 514/337; 514/470; 546/268.4; 546/284.1; 549/467

(58) Field of Classification Search ............. 546/268.4, 546/284.1; 549/467; 514/337, 470
See application file for complete search history.

(56) References Cited

U.S. PATENT DOCUMENTS

| 5,591,776 A | 1/1997 | Cavalla et al. |
| 5,622,977 A | 4/1997 | Warrellow et al. |
| 5,633,257 A | 5/1997 | Warrellow et al. |
| 5,679,696 A | 10/1997 | Fenton et al. |
| 5,693,659 A | 12/1997 | Head et al. |
| 5,698,711 A | 12/1997 | Palfreyman |
| 5,710,160 A | 1/1998 | Guay et al. |
| 5,710,170 A | 1/1998 | Guay et al. |
| 5,712,298 A | 1/1998 | Amschler |
| 5,723,460 A | 3/1998 | Warrellow et al. |
| 5,728,712 A | 3/1998 | Montana et al. |
| 5,739,144 A | 4/1998 | Warrellow et al. |
| 5,776,958 A | 7/1998 | Warrellow et al. |
| 5,780,477 A | 7/1998 | Head et al. |
| 5,780,478 A | 7/1998 | Alexander et al. |
| 5,786,354 A | 7/1998 | Warrellow et al. |
| 5,798,373 A | 8/1998 | Warrellow et al. |
| 5,814,651 A | 9/1998 | Duplantier et al. |
| 5,840,724 A | 11/1998 | Fenton et al. |
| 5,849,770 A | 12/1998 | Head et al. |
| 5,859,034 A | 1/1999 | Warrellow et al. |
| 5,866,593 A | 2/1999 | Warrellow et al. |
| 5,880,135 A | 3/1999 | Gully et al. |
| 5,889,014 A | 3/1999 | Cavalla et al. |
| 5,891,896 A | 4/1999 | Warrellow et al. |
| 5,919,937 A | 7/1999 | Lynch et al. |
| 5,935,978 A | 8/1999 | Fenton et al. |
| 5,962,483 A | 10/1999 | Warrellow et al. |
| 5,962,492 A | 10/1999 | Warrellow et al. |
| 6,040,329 A | 3/2000 | Marfat |
| 6,077,854 A | 6/2000 | Warrellow et al. |
| 6,096,768 A | 8/2000 | Ashton et al. |
| 6,153,630 A | 11/2000 | Cavalla et al. |
| 6,162,830 A | 12/2000 | Connor et al. |
| 6,180,650 B1 | 1/2001 | Frenette et al. |
| 6,200,993 B1 | 3/2001 | Cote et al. |
| 6,204,275 B1 | 3/2001 | Friesen et al. |
| 6,245,774 B1 | 6/2001 | Warrellow et al. |
| 6,255,326 B1 | 7/2001 | Ashton et al. |
| 6,262,040 B1 | 7/2001 | Marfat |
| 6,297,264 B1 | 10/2001 | Head et al. |

(Continued)

FOREIGN PATENT DOCUMENTS

EP  0994100 A1  4/2000

(Continued)

OTHER PUBLICATIONS

Golub et al., Science, 286, 531-537, Oct. 15, 1999.*

(Continued)

Primary Examiner—Fiona T. Powers
(74) Attorney, Agent, or Firm—Millen, White, Zelano & Branigan, P.C.

(57) ABSTRACT

PDE4 inhibition is achieved by novel compounds, e.g., aminoindazole and aminobenzofuran analogs. The compounds of the present invention are of Formulas I and II:

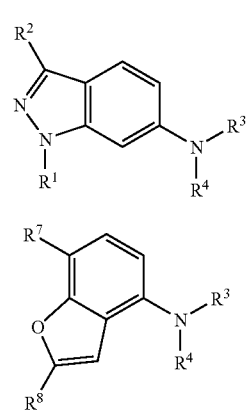

wherein $R^1$, $R^2$, $R^3$, $R^4$, $R^7$ and $R^8$ are as defined herein.

40 Claims, No Drawings

U.S. PATENT DOCUMENTS

| | | | |
|---|---|---|---|
| 6,699,890 B1 * | 3/2004 | Schumacher et al. | 514/352 |
| 2002/0151566 A1 | 10/2002 | Schumacher et al. | |
| 2004/0152902 A1 * | 8/2004 | Schumacher et al. | 546/275.7 |
| 2005/0119225 A1 * | 6/2005 | Schumacher et al. | 514/63 |

FOREIGN PATENT DOCUMENTS

| | | |
|---|---|---|
| EP | 1116711 A2 | 7/2001 |
| FR | 2729142 A1 | 7/1996 |
| JP | 11-189577 | 7/1999 |
| JP | 2001 011047 | 1/2001 |
| WO | WO 93/25517 | 12/1993 |
| WO | WO 94/02465 | 2/1994 |
| WO | WO 94/14742 | 7/1994 |
| WO | WO 94/27971 A1 | 12/1994 |
| WO | WO 95/01338 | 1/1995 |
| WO | WO 96 21435 | 7/1996 |
| WO | WO 96/21435 A1 | 7/1996 |
| WO | WO 96/23754 | 8/1996 |
| WO | WO 96/36620 | 11/1996 |
| WO | WO 97 00868 | 1/1997 |
| WO | WO 97 49702 | 12/1997 |
| WO | WO 98 09961 | 3/1998 |
| WO | WO 98/58901 | 12/1998 |
| WO | WO 99/33806 | 7/1999 |
| WO | WO 00/64874 | 11/2000 |
| WO | WO 00 69841 | 11/2000 |
| WO | WO 00/71129 A1 | 11/2000 |
| WO | WO 01/70738 | 9/2001 |
| WO | WO 02 059110 | 8/2002 |
| WO | WO 02 074726 | 9/2002 |

OTHER PUBLICATIONS

McGarry et al., Bioorganic and Medicinal Chemistry, 7, 1131-1139, 1999.*

Piaz et al., Eur. J. Med. Chem., 35, 463-480, 2000.*

Barnes, Peter J., Am. J. Respir. Crit. Care Med., 160, S72-S79, 1999.*

Giembycz, Mark A., Drugs, 59(2), 193-212, Feb. 2000.*

Heilman et al, "Synthesis and Antiinflammatory Evaluation of Substitued Isophthalonitriles, Trimesonitriles, Benzonitriles, and Terephthalonitriles", Journal of Medicinal Chemistry, 1978, vol. 21, No. 9, pp. 906-913, XP-002226236.

Watanabe et al, "Structure-Activity Relationship and Rational Design of 3,4-Dephostatin Derivatives as Protein Tyrosine Phosphatase Inhibitors", Pergamon Tetrahedron, 2000, vol. 56, pp. 741-752.

Inoue et al, "Steric Tuning in Chiral Ligand Mediated Enantioselective Alkylation of Imines", Tetrahedron: Asymmetry, 1993, vol. 4, No.7, pp. 1603-1606, XP002226237.

Thomas C. McKenzie et al., "The Gomberg-Bachmann Reaction of Purines", J. Heterocyclic Chem., May-Jun. 1987, pp. 859-861, vol. 24.

Vasu Nair et al., "Novel, Stable Congeners of Antiretroviral Compound 2', 3'-Dideoxyadenosine," J. Am. Chem. Soc., 1989, pp. 8502-8504, vol. 111.

Vasu Nair et al., "Synthesis Of Congeners Of Adenosine Resistant To Deamination By Adenosine Deaminase," J. Chem. Soc Comm., 1989, pp. 878-879.

James L. Kelley et al., "Synthesis and Structure- Activity Relationships of 2-Substituted-6-(dimethylamino)-9-(4-methylbenzyl)-9H-purines with Antirhinovirus Activity," J. Med. Chem., 1989, pp. 218-224, vol. 32.

James E. Kelley et al., "Antirhinovirus structure-activity relationships of 6-substituted-9-(4-methylbenzyl)-2-trifluoromethyl-9H-purines," Eur. J. Med. Chem., 1990, pp. 131-135, vol. 25.

Roger J. Schilling et al., "A High-Throughput Assay For Cyclic Nucleotide Phosphodiesterases," Analytical Biochemistry, 1994, pp. 154-158, vol. 215.

Donald V. Daniels et al., "A Semiautomated Method for the Assay of Cyclic Adenosine 5'-Monophosphate Phosphodiesterase," Analytical Biochemistry, 1996, pp. 367-369, vol. 236.

Jean-Jacques Bourguignon et al., "9-Benzyladenines: Potent and Selective cAMP Phosphodiesterase Inhibitors," J. Med. Chem, 1997, pp. 1768-1770, vol. 40.

James L. Kelley et al., "6-(Alkylamino)-9-alkylpurines. A New Class of Potential Antipsychotic Agents," J. Med. Chem., 1997, pp. 3207-3216, vol. 40.

Hiroyuki Sawanishi et al., "Selective Inhibitors of Cyclic AMP-Specific Phosphodiesterase: Heterocycle-Condensed Purines", J. Med. Chem., 1997, pp. 3248-3253, vol. 40.

J.E. Sounnes et al., "Proposal for Pharmacologically Distinct Conformers of PDE4 Cyclic AMP Phosphodiesterases", Cell Signal, 1997, pp. 227-236. vol. 9, No. 3-4.

Mary Elizabeth Bach et al., "Age-related defects in spatial memory are correlated with defects in the late phase of hippocampal long term potentiation in vitro and are attenuated by drugs that enhance the cAMP signaling pathway", Proc. Natl. Acad. Sci. USA, Apr. 1999, pp. 5280-5285, vol. 96.

Elisabeth Boichot et al., "Anti-Inflammatory Activities of a New Series of Selective Phosphodiesterase 4 Inhibitors Derived from 9-Benzyladenine," The Journal Of Pharmacology And Experimental Therapeutics, 2000, pp. 647-653, vol. 292, No. 2.

Anil S. Guram et al., "A Simple Catalytic Method for the conversion of Aryl Bromides to Arylamines," Angew. Chem. Int, Ed. Engl., 1995, vol. 34, No. 12, pp. 1348-1350.

Michael S. Driver et al., "A Second-Generation Catalyst for the Aryl Halide Amination: Mixed Secondary Amines from Aryl Halides and Primary Amines Catalyzed by (DPPF)PdCl$_2$, " J. Am. Chem. Soc., 1996, vol. 118, pp. 7217-7218.

Takashi Egawa et al., "Rolipram and its Optical Isomers, Phosphodiesterase 4 Inhibitors, Attenuated the Scopolamine-Induced Impairments of Learning and Memory in Rats," J. Pharmacol., vol. 75, 275-281(1997).

Peng Wang et al., "Expression, Purification, and Characterization of Human cAMP-Specific Phosphodiesterase (PDE4) Subtypes A, B, C, and D,"Biochem. And Biophys. Research Comm., vol. 234, 320-324 (1997).

Domine M. T. Chan et al., "New N- abd O-Arylations with Phenylboronic Acids and Cupric Acetate," Tetrahedron Letters, vol. 39, 2933-2936 (1998).

Mark Barad et al., "Rolipram, a Type IV-Specific Phosphodiesterase Inhibitor Facillitates the Establishment of Long-lasting Long-term Potentiation and Improves Memory," Proc. Natl. Acad. Sci., vol. 95, pp. 15020-15025 (Dec. 1998).

Miles D. Houslay et al., "The Multienzyme PDE4 Cyclic Adenosine Monophosphate-Specific Phosphodiesterase Family: Intracelllular Targeting, Regulation, and Selective Inhibition by Compounds Exerting Anti-inflammatory and Antidepressant Actions," Advances in Pharmacology, vol. 44, pp. 225-342, 1998.

John Hartwig et al., "Room-Temperature Palladium-Catalyzed Amination of Aryl Bromides and Chlorides and Extended Scope of Aromatic C-N Bond Formation with a Commercial Ligand," J. Org. Chem., 1999, vol. 64, pp. 5575-5580.

Han-Ting Zhang et al., "Inhibition of Cyclic AMP Phosphodiesterase (PDE4) Reverses Memory Deficits Associated with NDMA Receptor Antagonism," Neuropsychopharmacology, 2000, vol. 23, pp. 198-204.

Han-Ting Zhang et al., "Effects of Rolipram on Scopolamine-induced Impairment of Working and Reference Memory in the Radial-arm Maze tests in Rats," Psychopharmacology (Berl) Jun. 2000;150(3):pp. 311-316.

T.W. Greene et al., Protective Groups in Organic Synthesis, 3$^{rd}$ Edition, Chapter 3, "Protection for Phenols and Catechols," pp. 246-292, John Wiley & Sons, 1999.

Japanese Patent Abstract No. 7206789 dated Aug. 8, 1995.

* cited by examiner

PHOSPHODIESTERASE 4 INHIBITORS, INCLUDING AMINOINDAZOLE AND AMINOBENZOFURAN ANALOGS

This application claims the benefit of U.S. Provisional Application No. 60/396,726, filed Jul. 19, 2002. This application is related to application Ser. No. 10/051,309 and its provisional applications, Ser. No. 60/262,651, filed Jan. 22, 2001, Ser. No. 60/267,196, filed Feb. 8, 2001, and Ser. No. 60/306,140, filed Jul. 14, 2001, their disclosures being hereby incorporated by reference in their entirety.

FIELD OF THE INVENTION

The present invention relates generally to the field of phosphodiesterase 4 (PDE4) enzyme inhibition. More specifically this invention relates to selective PDE4 inhibition by novel compounds, e.g., aminoindazole and aminobenzofuran analogs, methods of preparing such compounds, compositions containing such compounds, and methods of use thereof.

BACKGROUND OF THE INVENTION

The cyclic nucleotide specific phosphodiesterases (PDEs) represent a family of enzymes that catalyze the hydrolysis of various cyclic nucleoside monophosphates (including cAMP and cGMP). These cyclic nucleotides act as second messengers within cells, and as messengers, carry impulses from cell surface receptors having bound various hormones and neurotransmitters. PDEs act to regulate the level of cyclic nucleotides within cells and maintain cyclic nucleotide homeostasis by degrading such cyclic mononucleotides resulting in termination of their messenger role.

PDE enzymes can be grouped into eleven families according to their specificity toward hydrolysis of cAMP or cGMP, their sensitivity to regulation by calcium, calmodulin or cGMP, and their selective inhibition by various compounds. For example, PDE 1 is stimulated by $Ca^{2+}$/calmodulin. PDE 2 is cGMP-dependent, and is found in the heart and adrenals. PDE 3 is cGMP-dependent, and inhibition of this enzyme creates positive inotropic activity. PDE 4 is cAMP specific, and its inhibition causes airway relaxation, antiinflammatory and antidepressant activity. PDE 5 appears to be important in regulating cGMP content in vascular smooth muscle, and therefore PDE 5 inhibitors may have cardiovascular activity. Since the PDEs possess distinct biochemical properties, it is likely that they are subject to a variety of different forms of regulation.

PDE4 is distinguished by various kinetic properties including low Michaelis constant for cAMP and sensitivity to certain drugs. The PDE4 enzyme family consists of four genes, which produce 4 isoforms of the PDE4 enzyme designated PDE4A, PDE4B, PDE4C, and PDE4D [See: Wang et al., Expression, Purification, and Characterization of human cAMP-Specific Phosphodiesterase (PDE4) Subtypes A, B, C, and D, *Biochem. Biophys. Res. Comm.*, 234, 320–324 (1997)] In addition, various splice variants of each PDE4 isoform have been identified.

PDE4 isoenzymes are localized in the cytosol of cells and are unassociated with any known membranous structures. PDE4 isoenzymes specifically inactivate cAMP by catalyzing its hydrolysis to adenosine 5'-monophosphate (AMP). Regulation of cAMP activity is important in many biological processes, including inflammation and memory. Inhibitors of PDE4 isoenzymes such as rolipram, piclamilast, CDP-840 and ariflo are powerful antiinflammatory agents and therefore may be useful in treating diseases where inflammation is problematic such as asthma or arthritis. Further, rolipram improves the cognitive performance of rats and mice in learning paradigms.

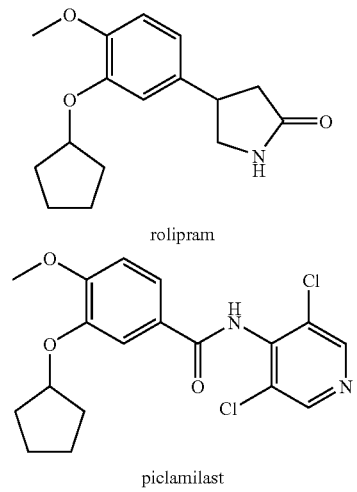

rolipram piclamilast

In addition to such compounds as rolipram, xanthine derivatives such as pentoxifylline, denbufylline, and theophylline inhibit PDE4 and have received considerable attention of late for their cognition enhancing effects. cAMP and cGMP are second messengers that mediate cellular responses to many different hormones and neurotransmitters. Thus, therapeutically significant effects may result from PDE inhibition and the resulting increase in intracellular cAMP or cGMP in key cells, such as those located in the nervous system and elsewhere in the body.

Rolipram, previously in development as an anti-depressant, selectively inhibits the PDE4 enzyme and has become a standard agent in the classification of PDE enzyme subtypes. Early work in the PDE4 field focused on depression and inflammation, and has subsequently been extended to include indications such as dementia. [see "The PDE IV Family Of Calcium-Phosphodiesterases Enzymes," John A. Lowe, III, et al., Drugs of the Future 1992, 17(9):799–807 for a general review). Further clinical developments of rolipram and other first-generation PDE4 inhibitors were terminated due to the side effect profile of these compounds. The primary side effect in primates is emesis, while the primary side effects in rodents are testicular degranulation, weakening of vascular smooth muscle, psychotrophic effects, increased gastric acid secretion and stomach erosion.

SUMMARY OF THE INVENTION

The present invention relates to novel compounds, e.g., aminoindazole and aminobenzofuran analogs, that inhibit PDE4 enzymes, and especially have improved side effect profiles, e.g., are relatively non-emetic, (e.g., as compared to the previously discussed prior art compounds). Preferably, the compounds selectively inhibit PDE4 enzymes. The compounds of this invention at the same time facilitate entry into cells, especially cells of the nervous system.

Still further, the present invention provides methods for synthesizing compounds with such activity and selectivity as well as methods of (and corresponding pharmaceutical compositions for) treating a patient, e.g., mammals, including humans, requiring PDE inhibition, especially PDE4 inhibition, for a disease state that involves elevated intracellular PDE 4 levels or decreased cAMP levels, e.g., involving neurological syndromes, especially those states associated with memory impairment, most especially long term memory impairment, as where such memory impairment is due in part to catabolism of intracellular cAMP levels by PDE 4 enzymes, or where such memory impairment may be improved by effectively inhibiting PDE4 enzyme activity.

In a preferred aspect, the compounds of the invention improve such diseases by inhibiting PDE4 enzymes at doses which do not induce emesis.

The present invention includes compounds of Formulas I and II:

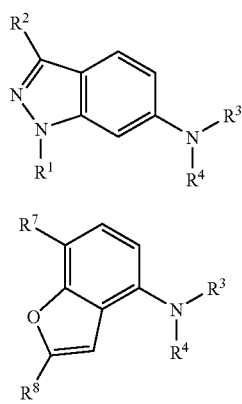

wherein
$R^1$ is H,
  alkyl having 1 to 8 carbon atoms, which is branched or unbranched and which is unsubstituted or substituted one or more times by halogen,
  cycloalkyl having 3 to 10, preferably 3 to 8 carbon atoms, which is unsubstituted or substituted one or more times by halogen, hydroxy, oxo, cyano, alkyl having 1 to 4 carbon atoms, alkoxy having 1 to 4 carbon atoms, or combinations thereof (e.g., cyclopentyl), or
  a heterocyclic group, which is saturated, partially saturated or unsaturated, having 5 to 10 ring atoms in which at least 1 ring atom is a N, O or S atom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl (eg., hydroxymethyl), hydroxamic acid, tetrazole-5-yl, hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, phenoxy, or combinations thereof (e.g., tetrahydrofuranyl, pyridyl, thienyl, pyrazinyl, quinolinyl, isoquinolinyl, pyrimidinyl, imidazolyl, thiazolyl, etc.),
$R^2$ is H, or
  alkyl having 1 to 4 carbon atoms, which is branched or unbranched and which is unsubstituted or substituted one or more times by halogen, cyano, and/or $C_{1-4}$-alkoxy (e.g., $CH_3$, $C_2H_5$, $CHF_2$, $CF_3$, etc.), and one or more —$CH_2CH_2$— groups can be replaced in each case by —CH=CH— or —C≡C—,
$R^3$ is H,
  alkyl having 1 to 8, preferably 1 to 4 carbon atoms, which is branched or unbranched and which is unsubstituted or substituted one or more times with halogen, cyano, $C_{1-4}$-alkoxy, or combinations thereof (e.g., methyl, ethyl, propyl, etc.),
  a partially unsaturated carbocycle-alkyl group wherein the carbocyclic portion has 5 to 14 carbon atoms and the alkyl portion which is branched or unbranched has 1 to 5 carbon atoms, and which is unsubstituted or substituted in the carbocyclic portion one or more times by halogen, alkyl, alkoxy, nitro, cyano, oxo, or combinations thereof, and the alkyl portion is optionally substituted by halogen, $C_{1-4}$-alkoxy, cyano or combinations thereof (e.g., cyclohexenylmethyl, etc.),
  arylalkyl having 7 to 19 carbon atoms, wherein the aryl portion has 6 to 14 carbon atoms and the alkyl portion, which is branched or unbranched, has 1 to 5 carbon atoms, arylalkyl radical is unsubstituted or substituted, in the aryl portion, one or more times by halogen, trifluoromethyl, $CF_3O$, nitro, amino, alkyl, alkoxy, alkylamino, dialkylamino and/or substituted in the alkyl portion by halogen, cyano, or methyl (e.g., benzyl, phenethyl, phenpropyl, methylbenzyl, methoxybenzyl, trfluoromethyl, benzyl, methylenedioxobenzyl, etc.), or heteroarylalkyl group, wherein the heteroaryl portion may be partially or fully saturated and has 5 to 10 ring atoms in which at least 1 ring atom is a N, O or S atom, the alkyl portion, which is branched or unbranched, has 1 to 5 carbon atoms, the heteroarylalkyl group is unsubstituted or substituted one or more times in the heteroaryl portion by halogen, alkyl, alkoxy, cyano, trifluoromethyl, $CF_3O$, nitro, oxo, amino, alkylamino, dialkylamino, or combinations thereof and/or substituted in the alkyl portion by halogen, cyano, or methyl or combinations thereof (e.g., pyridylmethyl, pyridylpropyl, methylpyridylmethyl, chloropyridylmethyl, dichloropyridylmethyl, thienylmethyl, thiazolylmethyl, quinolinylmethyl, isoquinolinylmethyl, piperidinylmethyl, furanylmethyl, imidazolylmethyl, methylimidazolylmethyl, pyrrolylmethyl, etc.);
$R^4$ is H,
  aryl having 6 to 14 carbon atoms and which is unsubstituted or substituted one or more times by halogen, alkyl, alkenyl, alkynyl, hydroxy, alkoxy, alkoxyalkoxy, nitro, methylenedioxy, ethylenedioxy, trifluoromethyl, $OCF_3$, amino, aminoalkyl, aminoalkoxy dialkylamino, hydroxyalkyl (eg., hydroxymethyl), hydroxamic acid, tetrazole-5-yl, 2(-heterocycle)tetrazole-5-yl (eg., 2-(2-tetrahydropyranyl)tetrazole-5-yl), hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, phenoxy, trialkylsilyloxy (eg. tert-butyldimethylsilyloxy), $R^5$-L-, or combinations thereof (e.g., substituted or unsubstituted phenyl, naphthyl, and biphenyl, such as phenyl, methylphenyl, chlorophenyl, fluorophenyl, vinylphenyl, cyanophenyl, methylenedioxophenyl, ethylphenyl, dichlorophenyl, carboxyphenyl, ethoxycarbonylphenyl, dimethylphenyl, hydroxymethylphenyl, nitrophenyl, aminophenyl, etc.), or heteroaryl having 5 to 10 ring atoms in which at least 1 ring atom is a heteroatom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl (eg., hydroxymethyl), hydroxamic acid, tetrazole-5-yl, hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, phenoxy, trialkylsilyloxy (eg. tert-butyldimethylsilyloxy), $R^5$-L-, or combinations thereof (e.g., pyridyl, thienyl, pyrazinyl, quinolinyl, isoquinolinyl, pyrimidinyl, imidazolyl, thiazolyl, etc.);

$R^5$ is H,
alkyl having 1 to 8, preferably 1 to 4 carbon atoms, which is unsubstituted or substituted one or more times with halogen, $C_{1-4}$-alkyl, $C_{1-4}$-alkoxy, oxo, or combinations thereof (e.g., methyl, ethyl, propyl, etc.),
alkylamino or dialkylamino wherein each alkyl portion has independently 1 to 8, preferably 1 to 4 carbon atoms (e.g., dimethylamino, etc.),
a partially unsaturated carbocycle-alkyl group wherein the carbocyclic portion has 5 to 14 carbon atoms and the alkyl portion has 1 to 5 carbon atoms, which is unsubstituted or substituted, preferably in the carbocyclic portion, one or more times by halogen, alkyl, alkoxy, nitro, cyano, oxo, or combinations thereof (e.g., cyclohexenylmethyl, etc.), cycloalkyl having 3 to 10, preferably 3 to 8 carbon atoms, which is unsubstituted or substituted one or more times by halogen, hydroxy, oxo, cyano, alkoxy, alkyl having 1 to 4 carbon atoms, or combinations thereof (e.g., cyclopentyl), cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, alkyl, alkoxy or combinations thereof (e.g., cyclopentylmethyl, cyclopropylmethyl, etc.),
aryl having 6 to 14 carbon atoms and which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl (eg., hydroxymethyl), hydroxamic acid, tetrazole-5-yl, hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, (e.g., substituted or unsubstituted phenyl and naphthyl, methylphenyl, chlorophenyl, fluorophenyl, vinylphenyl, cyanophenyl, methylenedioxophenyl, ethylphenyl, dichlorophenyl, carboxyphenyl, ethoxycarbonylphenyl, dimethylphenyl, hydroxymethylphenyl, nitrophenyl, aminophenyl, etc.),
arylalkyl having 7 to 19 carbon atoms, wherein the aryl portion has 6 to 14 carbon atoms and the alkyl portion, which is branched or unbranched, has 1 to 5 carbon atoms, arylalkyl radical is unsubstituted or substituted, in the aryl portion, one or more times by halogen, trifluoromethyl, $CF_3O$, nitro, amino, alkyl, alkoxy, amino, alkylamino, dialkylamino and/or substituted in the alkyl portion by halogen, cyano, or methyl (e.g., benzyl, phenethyl, phenpropyl, methylbenzyl, methoxybenzyl, trfluoromethyl, benzyl, methylenedioxobenzyl, etc.),
a heterocyclic group, which is saturated, partially saturated or unsaturated, having 5 to 10 ring atoms in which at least 1 ring atom is a N, O or S atom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl (eg., hydroxymethyl), hydroxamic acid, tetrazole-5-yl, hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, phenoxy, or combinations thereof (e.g., pyridyl, thienyl, pyrazinyl, quinolinyl, isoquinolinyl, pyrimidinyl, imidazolyl, thiazolyl, etc.), or a heterocycle-alkyl group, wherein the heterocyclic portion is saturated, partially saturated or unsaturated, and has 5 to 10 ring atoms in which at least 1 ring atom is a N, O or S atom, and the alkyl portion which is branched or unbranched and has 1 to 5 carbon atoms, the heterocycle-alkyl group is unsubstituted or substituted one or more times in the heterocyclic portion by halogen, alkyl, alkoxy, cyano, trifluoromethyl, $CF_3O$, nitro, oxo, amino, alkylamino, dialkylamino, or combinations thereof and/or substituted in the alkyl portion by halogen, cyano, or methyl or combinations thereof (e.g., pyridylmethyl, pyridylpropyl, methylpridylmethyl, etc.);

L is a single bond or a divalent aliphatic radical having up to 8 carbon atoms wherein one or more —$CH_2$— groups are each optionally replaced by —O—, —S—, —$SO_2$—, —SO—, —$NR^6$—, —$SO_2NH$—, —$NHSO_2$—, —CO—, —$NR^6CO$—, —$CONR^6$—, —NHCONH—, —OCONH, —NHCOO—, —SCONH—, —SCSNH—, or —NHCSNH— (e.g., —O—, —$CH_2$—, —CO—, —CO—O—, —O—CO—, —CO—NH—, —NH—CO—, —$CH_2CH_2CH_2$—NH—CO—, —$CH_2$—$CH_2$—O—, —$SO_2$—NH—$CH_2CH_2$—O—, —O—$CH_2CH_2$—O—, —$CH_2$—NH—CO—, —CO—NH—$CH_2$—, —$SO_2$—NH—, —$CH_2$—NH—$SO_2$—, —$CH_2CH_2CH_2$—$SO_2$—NH—, —$CONHSO_2$—, etc.);

$R^6$ is H,
alkyl having 1 to 8, preferably 1 to 4 carbon atoms, which is branched or unbranched and which is unsubstituted or substituted one or more times with halogen, $C_{1-4}$-alkyl, $C_{1-4}$-alkoxy, oxo, or combinations thereof (e.g., methyl, ethyl, propyl, etc.);

$R^7$ is alkoxy or alkylthio, in each case having 1 to 4 carbon atoms, which is branched or unbranched and which is unsubstituted or substituted one or more times by halogen (e.g., $CH_3$, $CHF_2$, $CF_3$, etc.), $R^8$ is —CO—$C_{1-4}$-alkyl which is branched or unbranched and which is unsubstituted or substituted one or more times by halogen (e.g., $CH_3$, $CHF_2$, $CF_3$, etc.), or is

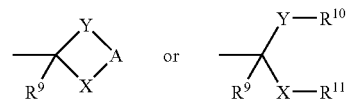

$R^9$ is H or alkyl having 1 to 4 carbon atoms, which is branched or unbranched, and which is unsubstituted or substituted one or more times by halogen (e.g., $CH_3$, $CHF_2$, $CF_3$, etc.), $R^{10}$ is alkyl having 1 to 6 carbon atoms, which is branched or unbranched, and which is unsubstituted or substituted one or more times by halogen (e.g., $CH_3$, $CHF_2$, $CF_3$, etc.), $R^{11}$ is alkyl having 1 to 6 carbon atoms, which is branched or unbranched, and which is unsubstituted or substituted one or more times by halogen (e.g., $CH_3$, $CHF_2$, $CF_3$, etc.), X and Y are each independently O or S, and A is alkylene having 2 to 7 carbon atoms which is unsubstituted or substituted one or more times by halogen;

wherein in Formula I both of $R^3$ and $R^4$ are other than H and in Formula II at least one of $R^3$ and $R^4$ is other than H; and pharmaceutically acceptable salts thereof.

According to a further aspect of the invention there is provided a genus of novel compounds according to the formulas III and IV:

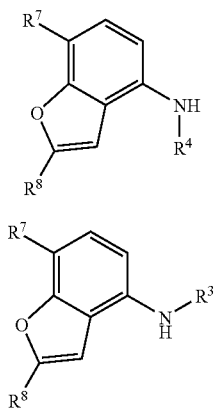

wherein $R^1$, $R^2$, $R^3$, $R^4$, $R^7$ and $R^8$ are as defined above. The compounds of this subgenus of Formulae I and II not only have PDE4 inhibitory activity, but also are useful as intermediates for preparing compounds of Formula II in which $R^3$ and $R^4$ are both other than H.

In addition, preferred compounds of Formulas I and II are those of subformulas V and VI

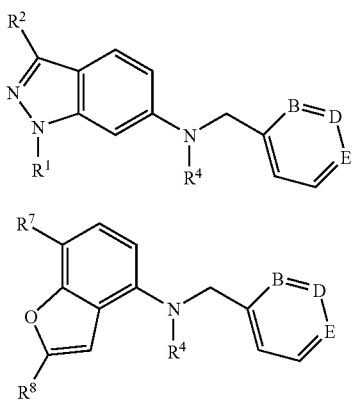

wherein $R^1$, $R^2$, $R^4$, $R^7$ and $R^8$ are as defined in Formulas I and II and one of B, D and E is N and the others are C. Preferably, D is N. Also, $R^4$ is preferably pyridyl or phenyl which in each case is substituted or unsubstituted.

In accordance with a further aspect of the invention the compounds of formulas I and II are selected from the following compounds:

7-Methoxy-2-(2-methyl-(1,3-dioxolane-2-yl))-4-[N-(4-pyridylmethyl)]aminobenzofuran,
7-Methoxy-2-(2-methyl-(1,3-dioxolane-2-yl))-4-[N-(3-pyridylmethyl)]aminobenzofuran,
7-Methoxy-2-(2-methyl-(1,3-dioxolane-2-yl))-4-[N-phenyl-N-(4-pyridylmethyl)]aminobenzofuran,
7-Methoxy-2-(2-methyl-(1,3-dioxolane-2-yl))-4-[N-(3-cyanophenyl)-N-(3-pyridylmethyl)]aminobenzofuran,
7-Methoxy-2-(2-methyl-(1,3-dioxolane-2-yl))-4-[N-phenyl-N-(3-pyridylmethyl)]aminobenzofuran,
7-Methoxy-2-(2-methyl-(1,3-dioxolane-2-yl))-4-[N-(3-cyanophenyl)-N-(4-pyridylmethyl)]aminobenzofuran,
7-Methoxy-2-(2-methyl-(1,3-dioxolane-2-yl))-4-[N-(4-acetylphenyl)-N-(3-pyridylmethyl)]aminobenzofuran,
7-Methoxy-2-(2-methyl-(1,3-dioxolane-2-yl))-4-[N-(4-carboxyphenyl)-N-(3-pyridylmethyl)]aminobenzofuran,
7-Methoxy-2-(2-methyl-(1,3-dioxolane-2-yl))-4-[N-(4-(2H-tetrazol-5-yl)phenyl)-N-(3-pyridylmethyl)]aminobenzofuran,
7-Methoxy-2-(2-methyl-(1,3-dioxolane-2-yl))-4-[N-(4-carboxy-3-chlorophenyl)-N-(3-pyridylmethyl)]aminobenzofuran,
7-Methoxy-2-(2-methyl-(1,3-dioxolane-2-yl))-4-[N-(3-carboxy-5-fluorophenyl)-N-(3-pyridylmethyl)]aminobenzofuran,
1-Cyclopentyl-6-[N-(3-(1,1-dimethylethoxycarbonyl)phenyl)-N-(3-pyridylmethyl)]-1H-aminoindazole,
2-Acetyl-7-methoxy-4-(N-(4-cyanophenyl)-N-(3-pyridylmethyl))aminobenzofuran,
2-Acetyl-7-methoxy-4-(N-phenyl-N-(4-pyridylmethyl))aminobenzofuran,
1-Cyclopentyl-6-(N-phenyl-N-(3-pyridylmethyl))aminoindazole,
1-Cyclopentyl-6-N-(3-carboxyphenyl)-N-(3-pyridylmethyl))aminoindazole,
2-Acetyl-7-methoxy-4-(N-(3-carboxyphenyl)-N-(3-pyridylmethyl))aminobenzofuran,
7-Methoxy-2-(2-methyl-(1,3-dioxolane-2-yl))-4-(N-(4-cyanophenyl)-N-(3-pyridylmethyl))-aminobenzofuran,
2-Acetyl-7-methoxy-4-(N-(3-cyanophenyl)-N-(3-pyridylmethyl))aminobenzofuran,
2-Acetyl-7-methoxy-4-(N-phenyl-N-(3-pyridylmethyl))aminobenzofuran,
2-Acetyl-7-methoxy-4-(N-(3-cyanophenyl)-N-(4-pyridylmethyl))aminobenzofuran,
2-Acetyl-7-methoxy-4-(N-(4-acetylphenyl)-N-(3-pyridylmethyl))aminobenzofuran,
2-Acetyl-7-methoxy-4-[N-(4-carboxyphenyl)-N-(3-pyridylmethyl)]aminobenzofuran,
2-Acetyl-7-methoxy-4-[N-(4-(2H-tetrazol-5-yl)phenyl)-N-(3-pyridylmethyl]aminobenzofuran,
2-Acetyl-7-methoxy-4-[N-(4-carboxy-3-chlorophenyl)-N-(3-pyridylmethyl)]aminobenzofuran,
2-Acetyl-7-methoxy-4-[N-(3-carboxy-5-fluorophenyl)-N-(3-pyridylmethyl)]aminobenzofuran,
6-Amino-1-cyclopentyl-3-ethyl-6-[N-3-(1,1-dimethylethoxycarbonyl)phenyl]-N-(3-pyridylmethyl)amino-1H-indazole,
1-Cyclopentyl-3-ethyl-6-[N-(3-carboxyphenyl)-N-(3-pyridylmethyl)]amino-1H-indazole,
2-Acetyl-7-methoxy-N-(4-phenylsulfonylaminocarbonylphenyl)-N-(3-pyridylmethyl)-4-aminobenzofuran, and pharmaceutically acceptable salts thereof, wherein optically active compounds can be in the form of their separate enantiomers or mixtures thereof, including racemic mixtures.

The compounds of the present invention are effective in inhibiting, or modulating the activity of PDE4 in animals, e.g., mammals, especially humans. These compounds exhibit neurological activity, especially where such activity affects cognition, including long term memory. These compounds will also be effective in treating diseases where decreased cAMP levels are involved. This includes but is not limited to inflammatory diseases. These compounds may also function as antidepressants, or be useful in treating cognitive and negative symptoms of schizophrenia.

Assays for determining PDE inhibiting activity as well as selectivity of PDE 4 inhibiting activity and selectivity of inhibiting PDE 4 isoenzymes are known within the art. See, e.g., U.S. Pat. No. 6,136,821, the disclosure of which is incorporated herein by reference.

According to a further aspect of the invention there are provided compounds useful as intermediates for the production of the PDE4 inhibitors described herein (e.g., PDE4 inhibitors of Formulas I and II) and/or useful for the synthesis of radio-labeled analogs of the PDE4 inhibitors with in this application.

Thus, there are provided intermediate compounds which correspond to compounds of Formulas I and II, wherein $R^2$, $R^3$, $R^4$ and $R^8$ are as previously defined for Formulas I and II, but $R^1$ or $R^7$ is H, tert-butyldimethylsilyl-, or a suitable phenolic or indazolyl protecting group. Suitable protecting groups are described, for example, in Greene, T. W. and Wuts, P. G. M., Protective Groups in Organic Synthesis, $3^{rd}$ Edition, John Wiley & Sons, 1999, pp. 246–293. These intermediates are also useful for the synthesis of radio-labeled compounds, such as where $R^7$ is $^3H_3CO—$, $^2H_3CO—$, $^{14}CH_3—$ or $^{11}CH_3—$, for example by removing the protecting group and reacting the resultant compound in which $R^1$ or $R^7$ is H with suitable radio-labeled reagents. Such radio-labeled compounds are useful for determining compound tissue distribution in animals, in PET imaging studies, and for in vivo, ex vivo, and in vitro binding studies.

As previously described, compounds according to formula III, wherein $R^4$, $R^7$ and $R^8$ are as previously described are useful intermediates for the production of compounds according to formula II where in $R^3$ is other than H.

Also, as previously described, compounds according to formula IV, wherein $R^3$, $R^7$ and $R^8$ are as previously described are useful intermediates for the production of compounds according to formula II where in $R^4$ is other than H.

Halogen herein refers to F, Cl, Br, and I. Preferred halogens are F and Cl.

Alkyl, as a group or substituent per se or as part of a group or substituent (e.g., alkylamino, trialkylsilyloxy, aminoalkyl, hydroxyalkyl), means a straight-chain or branched-chain aliphatic hydrocarbon radical having 1 to 12 carbon atoms, preferably 1 to 8 carbon atoms, especially 1 to 4 carbon atoms. Suitable alkyl groups include methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by halogens, oxo, hydroxyl, $C_{1-4}$-alkoxy and/or cyano. Halogens are preferred substituents, especially F and Cl.

Alkoxy means alkyl-O— groups and alkoxyalkoxy means alkyl-O-alkyl-O— groups in which the alkyl portions are in accordance with the previous discussion. Suitable alkoxy and alkoxyalkoxy groups include methoxy, ethoxy, propoxy, butoxy, pentoxy, hexoxy, heptoxy, octoxy methoxymethoxy ethoxymethoxy, propoxymethoxy, and methoxyethoxy. Preferred alkoxy groups are methoxy and ethoxy. Similarly, alkoxycarbonyl means alkyl —O—CO— in which the alkyl portion is in accordance with the previous discussion. Examples include methoxycarbonyl, ethoxycarbonyl, propoxycarbonyl, and tert-butoxycarbonyl.

Cycloalkyl means a monocyclic, bicyclic or tricyclic nonaromatic saturated hydrocarbon radical having 3 to 10 carbon atoms, preferably 3 to 8 carbon atoms, especially 3 to 6 carbon atoms. Suitable cycloalkyl groups include cyclopropyl, cyclobutyl, cyclopentyl, cyclohexyl, cycloheptyl, cyclooctyl, norbornyl, 1-decalin, adamant-1-yl, and adamant-2-yl. Other suitable cycloalkyl groups include spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, and spiro[3.5]nonyl. Preferred cycloalklyl groups are cyclopropyl, cyclopentyl and cyclohexyl. The cycloalkyl group can be substituted, for example, substituted by halogens and/or alkyl groups.

Cycloalkylalkyl refers to cycloalkyl-alkyl radicals in which the cycloalkyl and alkyl portions are in accordance with previous discussions. Suitable examples include cyclopropylmethyl and cyclopentylmethyl.

Aryl, as a group or substituent per se or as part of a group or substituent, refers to an aromatic carbocyclic radical containing 6 to 14 carbon atoms, preferably 6 to 12 carbon atoms, especially 6 to 10 carbon atoms. Suitable aryl groups include phenyl, naphthyl and biphenyl. Substituted aryl groups include the above-described aryl groups which are substituted one or more times by, for example, halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, and phenoxy.

Arylalkyl refers to an aryl-alkyl-radical in which the aryl and alkyl portions are in accordance with the previous descriptions. Suitable examples include benzyl, 1-phenethyl, 2-phenethyl, phenpropyl, phenbutyl, phenpentyl, and napthylmethyl.

Heteroaryl refers to an aromatic heterocyclic group having one or two rings and a total number of 5 to 10 ring atoms wherein at least one of the ring atoms is a heteroatom. Preferably, the heteroaryl group contains 1 to 3, especially 1 or 2, hetero-ring atoms which are selected from N, O and S. Suitable heteroaryl groups include furyl, thienyl, pyrrolyl, pyrazolyl, imidazolyl, triazolyl, tetrazolyl, dithialyl, oxathialyl, isoxazolyl, oxazolyl, thiazolyl, isothiazolyl, oxadiazolyl, oxatriazolyl, dioxazolyl, oxathiazolyl, thiadiazolyl, pyridyl, pyridazinyl, pyrimidinyl, pyrazinyl, triazinyl, oxazinyl, isoxazinyl, oxathiazinyl, oxadiazinyl, benzofuranyl, isobenzofuranyl, thionaphthenyl, isothionaphthenyl, indolyl, isoindolyl, indazolyl, benzisoxazolyl, benzoxazolyl, benzthiazolyl, benzisothiazolyl, purinyl, benzopyranyl, quinolinyl, isoquinolinyl, cinnolinyl, quinazolinyl, naphthyridinyl, and benzoxazinyl, e.g., 2-thienyl, 3-thienyl, 2-, 3- or 4-pyridyl, 2-, 3-, 4-, 5-, 6-, 7- or 8-quinolinyl, and 1-, 3-, 4-, 5-, 6-, 7- or 8-isoquinolinyl.

Substituted heteroaryl refers to the heteroaryl groups described above which are substitued in one or more places by, for example, halogen, aryl, alkyl, alkoxy, carboxy, methylene, cyano, trifluoromethyl, nitro, oxo, amino, alkylamino, and dialkylamino.

Heterocycles include heteroaryl groups as described above as well as non-aromatic cyclic groups containing at least one hetero-ring atom, preferably selected from N, S and O, for example, tetrahydrofuranyl, piperidinyl, and pyrrolidinyl.

Heterocycle-alkyl refers to a heterocycle-alkyl-group wherein the heterocyclic and alkyl portions are in accordance with the previous discussions. Suitable examples are pyridylmethyl, thienylmethyl, pyrimidinylmethyl, pyrazinylmethyl, and isoquinolinylmethyl.

Partially unsaturated carbocyclic structures are non-aromatic monocyclic or bicyclic structures containing 5 to 14 carbon atoms, preferably 6 to 10 carbon atoms, wherein the ring structure(s) contains at least one C=C bond. Suitable examples are cyclopentenyl, cyclohexenyl, cyclohexadienyl, tetrahydronaphthenyl and indan-2-yl.

Alkenyl refers to straight-chain or branched-chain aliphatic radicals containing 2 to 12 carbon atoms in which one or more —$CH_2$—$CH_2$— structures are each replaced by —CH=CH—. Suitable alkenyl groups are ethenyl, 1-propenyl, 2-methylethenyl, 1-butene, 2-butene, 1-pentenyl, and 2-pentenyl.

Alkynyl refers to straight-chain or branched-chain aliphatic radicals containing 2 to 12 carbon atoms in which one or more —$CH_2$—$CH_2$— structures are each replaced by —C≡C—. Suitable alkynyl groups are ethynyl, propynyl, 1-butynyl, and 2-butynyl.

Acyl refers to alkanoyl radicals having 1 to 13 carbon atoms in which the alkyl portion can be substituted by halogen, alkyl, aryl and/or alkoxy, or aroyl radicals having 7 to 15 carbon atoms in which the aryl portion can be substituted by, for example, halogen, alkyl and/or alkoxy. Suitable acyl groups include formyl, acetyl, propionyl, butanoyl and benzoyl.

Substituted radicals preferably have 1 to 3 substituents, especially 1 to 2 substituents.

In the compounds of Formula I, $R^1$ can be an alkyl group having preferably 2 to 4 carbon atoms which is optionally substituted by halogen, preferably fluorine or chlorine.

$R^1$ can also preferably be cycloalkyl, particularly cyclopentyl or cyclohexyl.

$R^2$ is preferably H or alkyl having 1 to 4 carbon atoms, especially $C_2H_5$.

$R^3$ is preferably hydrogen, alkyl having 1 to 4 carbon atoms (e.g., methyl, ethyl, n-propyl, or n-butyl), arylalkyl (e.g., substituted or unsubstitituted benzyl, phenethyl, and phenpropyl), or a heteroarylalkyl group (e.g., substituted or unsubstituted pyridylmethyl, furanylmethyl, thienylmethyl, pyrrolylmethyl, pyrimidinylmethyl, thiazolylmethyl, isoquinolinylmethyl and quinolinylmethyl). Preferred substituents for aryl and heteroaryl portions of $R^3$ are F, Cl, $CH_3$, $C_2H_5$, $OCH_3$, and CN. In particular, $R^3$ is preferably pyridylmethyl.

$R^4$ is preferably aryl, or heteroaryl, especially phenyl, naphthyl, biphenyl, furanyl, pyrazinyl, pyrimidinyl, pyridyl, quinolinyl, and isoquinolinyl, which in each case is unsubstituted or is substituted one or more times. Preferred substituents are OH, F, Cl, $CF_3$, alkyl (such as methyl or ethyl), alkoxy (such as methoxy and ethoxy), CN, vinyl, $CH_2OH$, CONHOH, $CONH_2$, methylenedioxy, COOH, and combinations thereof. For example, $R^4$ can be phenyl substituted by halogen, COOH and/or CN.

In addition, when $R^4$ is aryl, especially, phenyl, preferred substituents include $R^5$-L-, e.g., $R^5$—, $R^5$—O—, $R^5$—CO—, $R^5$—NH—CO—, $R^5$—$SO_2$—NH—, $R^5$—$SO_2$—NH-alkylene-O—, $NH_2$-alkyl-NH—CO—, $R^5$-alkylene-NH—CO—, alkyl-CO—NH-alkyl- as well as methyl, ethyl, Cl, F, CN, $OCH_3$, $CF_3$, amino, nitro, $HOCH_2$ and COOH.

When $R^4$ is aryl substituted by $R^5$—$SO_2$—NH— it is preferably a substituted phenyl group and $R^5$ is preferably methyl, ethyl, propyl or phenyl.

When $R^4$ is aryl substituted by $R^5$—$SO_2$—NH-alkylene-O— it is preferably a substituted phenyl. In such cases, $R^5$ is preferably methyl, ethyl, propyl or phenyl and alkylene is preferably —$CH_2$—, —$CH_2CH_2$— or —$CH_2CH_2CH_2$—.

When $R^4$ is aryl substituted by $R^5$-L- it is preferably substituted phenyl. In such cases, preferred $R^5$ groups include phenyl, tetrazolyl, oxazinyl, piperazinyl, methylpiperazinyl, pyridyl, methylpyridyl, pyrrolinyl, methylpyrrolinyl, piperadinyl, or methylpiperadinyl, and L is preferably a single bond, —O—, —CO—, —$CH_2$—, —$CH_2CH_2$—, —$CH_2CH_2CH_2$—, —$CH_2$—O—, —$CH_2CH_2$—O—, —$CH_2CH_2CH_2$—O—, —$CH_2$—NH—$CH_2CH_2$—O—, —CO—NH—, —NH—CO—, or —$CONHSO_2$—.

$R^7$ is preferably alkoxy having 1 to 4 carbon atoms, which is branched or unbranched and which is unsubstituted or substituted one or more times by halogen, e.g., $CH_3$ or $C_2H_5$.

$R^8$ is preferably —CO—$C_{1-4}$-alkyl, e.g., —$COCH_3$.

$R^9$ is preferably —$CH_3$.

X and Y are preferably both O or S, especially O.

A is preferably —$CH_2CH_2$—.

In addition, preferred PDE4 inhibitors in accordance with the invention are compounds described by subformulas Ia to IIe which correspond to formulas I and II but exhibit the following preferred groups:

Ia $R^3$ is arylalkyl or heteroarylalkyl, in each case substituted or unsubstituted; and
$R^4$ is H or is aryl or heteroaryl, in each case substituted or unsubstituted.

Ib $R^1$ is cycloalkyl; and
$R^2$ is H or $C_2H_5$.

Ic $R^1$ is cycloalkyl;
$R^2$ is H or $C_2H_5$;
$R^3$ is arylalkyl or heteroarylalkyl, in each case substituted or unsubstituted; and
$R^4$ is H or is aryl or heteroaryl, in each case substituted or unsubstituted.

Id $R^1$ is cyclopentyl;
$R^2$ is H or $C_2H_5$;
$R^3$ is arylalkyl or heteroarylalkyl, in each case substituted or unsubstituted; and
$R^4$ is H or is aryl or heteroaryl, in each case substituted or unsubstituted.

Ie $R^1$ is cyclopentyl;
$R^2$ is H or $C_2H_5$;
$R^3$ is pyridyl which is substituted or unsubstituted; and
$R^4$ is H or is aryl or heteroaryl, in each case substituted or unsubstituted.

If $R^1$ is cyclopentyl;
$R^2$ is H or $C_2H_5$;
$R^3$ is pyridyl which is substituted or unsubstituted; and
$R^4$ is phenyl which is substituted or unsubstituted.

IIa $R^3$ is arylalkyl or heteroarylalkyl, in each case substituted or unsubstituted; and
$R^4$ is H or is aryl or heteroaryl, in each case substituted or unsubstituted.

IIb $R^7$ is alkoxy having 1 to 4 carbon atoms;
$R^8$ is $COCH_3$ or

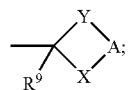

$R^9$ is —$CH_3$;
X and Y are both O or S; and
A is —$CH_2CH_2$—.

IIc $R^3$ is arylalkyl or heteroarylalkyl, in each case substituted or unsubstituted; and
$R^4$ is H or is aryl or heteroaryl, in each case substituted or unsubstituted;
$R^7$ is alkoxy having 1 to 4 carbon atoms;
$R^8$ is $COCH_3$ or

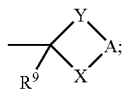

$R^9$ is —$CH_3$;
X and Y are both O or S; and
A is —$CH_2CH_2$—,

IId $R^3$ is pyridyl which is substituted or unsubstituted;
$R^4$ is H or is aryl or heteroaryl, in each case substituted or unsubstituted;
$R^7$ is alkoxy having 1 to 4 carbon atoms;
$R^8$ is $COCH_3$ or

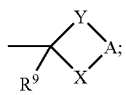

$R^9$ is —$CH_3$;
X and Y are both O or S; and
A is —$CH_2CH_2$—.

IIe $R^3$ is pyridyl which is substituted or unsubstituted;
$R^4$ is phenyl which is substituted or unsubstituted;
$R^7$ is alkoxy having 1 to 4 carbon atoms;
$R^8$ is $COCH_3$ or

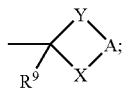

$R^9$ is —$CH_3$;
X and Y are both O or S; and
A is —$CH_2CH_2$—.

Preferred aspects include pharmaceutical compositions comprising a compound of this invention and a pharmaceutically acceptable carrier and, optionally, another active agent as discussed below; a method of inhibiting a PDE4 enzyme, especially an isoenzyme, e.g., as determined by a conventional assay or one described herein, either in vitro or in vivo (in an animal, e.g., in an animal model, or in a mammal or in a human); a method of treating neurological syndrome, e.g., loss of memory, especially long-term memory, cognitive impairment or decline, memory impairment, etc. a method of treating a disease state modulated by PDE4 activity, in a mammal, e.g., a human, e.g., those mentioned herein.

The compounds of the present invention may be prepared conventionally. All starting materials are known or can be conventionally prepared from known starting materials. Some of the processes which can be used are described below.

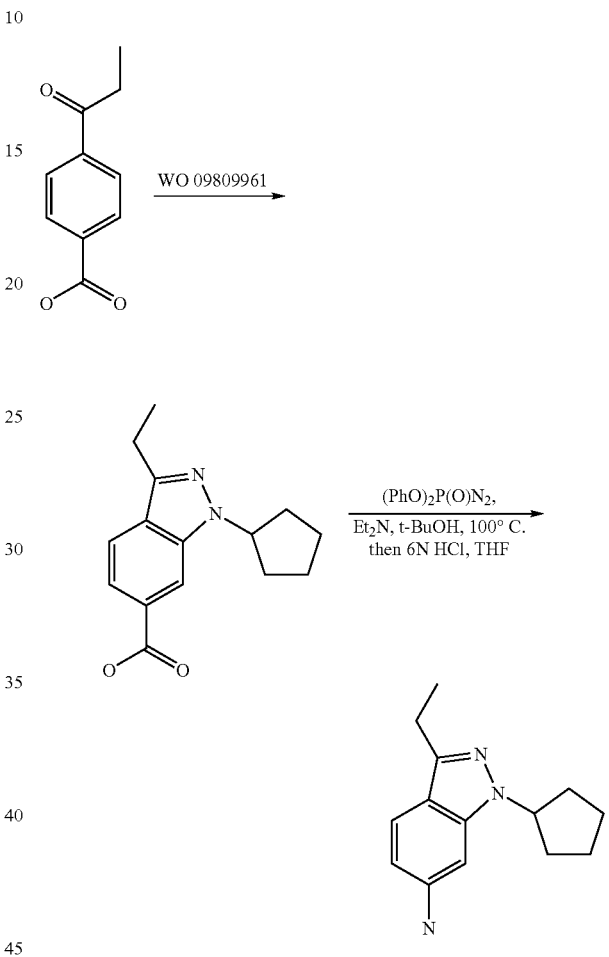

Starting material 6-amino-1-cyclopentyl-3-ethylindazole can be synthesized from the corresponding 6-carboxy-1-cyclopentyl-3-ethylindazole by a Curtius rearrangement. The starting 6-carboxy-1-cyclopentyl-3-ethylindazole can be prepared by methods common in the art (see, e.g., WO 098/09961). Alternatively, starting 6-amino-1-cyclopentyl-3-ethylindazoles can be synthesized by amination of 6-halo-1-cycloalkyl-3-ethylindazole or reduction of 6-nitro-1-cycloalkyl-3-etliylindazole. The indazole scaffold can be prepared by several methods common to the art, such as by reaction of cycloalkylhydrazine with 2,4-difluoropropiophenone.

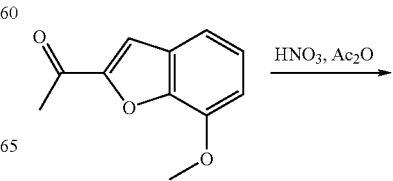

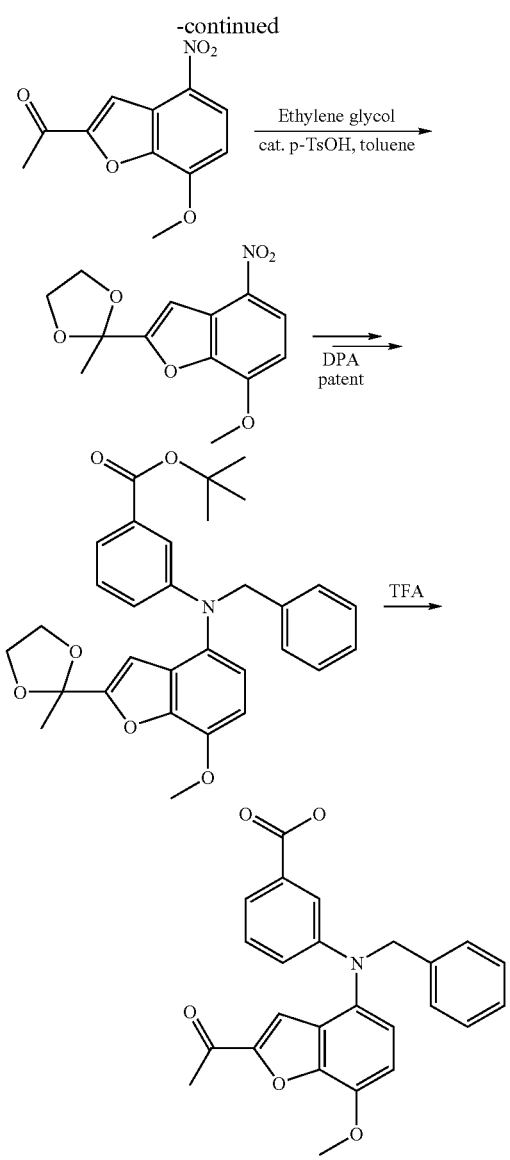

Starting benzofurans are either commercially available or can be synthesized according literature methods by intramolecular aldol condensation of appropriately substituted beta-ketoethers of salicylaldehydes. (see Strategies for Organic Drug Synthesis and Design, Daniel Lednicer, Ed., 1998, John Wiley and Sons, Inc. Chapter 10 pp. 286–289). Nitration of 2-acetyl-7-methoxybenzofuran with nitric acid in acetic anhydride provides 2-acetyl-7-methoxy-4-nitrobenzofuran. (in the above scheme, DPA patent refers to U.S. patent application Ser. No. 10/051,309).

Protection of the carbonyl group with a suitable base stable protecting group such as a dioxane or dioxolane provides the desired starting 4-nitrobenzofurans. See also WO 99/40085 and WO 99/37640.

One of ordinary skill in the art will recognize that some of the compounds of Formulas I and II can exist in different geometrical isomeric forms. In addition, some of the compounds of the present invention possess one or more asymmetric carbon atoms and are thus capable of existing in the form of optical isomers, as well as in the form of racemic or nonracemic mixtures thereof, and in the form of diastereomers and diastereomeric mixtures inter alia. All of these compounds, including cis isomers, trans isomers, diastereomic mixtures, racemates, nonracemic mixtures of enantiomers, and substantially pure and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formulae I and II can likewise be obtained by chiral syntheses utilizing optically active starting materials.

In addition, one of ordinary skill in the art will recognize that the compounds can be used in different enriched isotopic forms, e.g., enriched in the content of $^2H$, $^3H$, $^{11}C$ and/or $^{14}C$.

The present invention also relates to useful forms of the compounds as disclosed herein, such as pharmaceutically acceptable salts and prodrugs of all the compounds of the present invention. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, mangnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

The compounds of the invention can be administered alone or as an active ingredient of a formulation. Thus, the present invention also includes pharmaceutical compositions of compounds of Formulas I or II containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553–1593 (current edition).

In view of their high degree of PDE4 inhibition, the compounds of the present invention can be administered to anyone requiring or desiring PDE4 inhibition, and/or enhancement of cognition. Administration may be accomplished according to patient needs, for example, orally, nasally, parenterally (subcutaneously, intravenously, intramuscularly, intrastemally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents such as other agents used in the treatment of cognitive impairment and/or in the treatment of psychosis, e.g., other PDE4 inhibitors, calcium channel blockers, chloinergic drugs, adenosine receptor modulators, amphakines NMDA-R modulators, mGluR modulators, and cholinesterase inhibitors (e.g., donepezil, rivastigimine, and glanthanamine). In such combinations, each active ingredient can be administered either in accordance with their usual dosage range or a dose below its usual dosage range.

The present invention further includes methods of treatment that involve inhibition of PDE4 enzymes. Thus, the present invention includes methods of selective inhibition of PDE4 enzymes in animals, e.g., mammals, especially humans, wherein such inhibition has a therapeutic effect, such as where such inhibition may relieve conditions involving neurological syndromes, such as the loss of memory, especially long-term memory. Such methods comprise administering to an animal in need thereof, especially a mammal, most especially a human, an inhibitory amount of a compound, alone or as part of a formulation, as disclosed herein.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline.

Dementias are diseases that include memory loss and additional intellectual impairment separate from memory. The present invention includes methods for treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The present invention includes methods for dealing with memory loss separate from dementia, including mild cognitive impairment (MCI) and age-related cognitive decline. The present invention includes methods of treatment for memory impairment as a result of disease. In another application, the invention includes methods for dealing with memory loss resulting from the use of general anesthetics, chemotherapy, radiation treatment, post-surgical trauma, and therapeutic intervention.

The compounds may be used to treat psychiatric conditions including schizophrenia, bipolar or manic depression, major depression, and drug addiction and morphine dependence. These compounds may enhance wakefulness. PDE4 inhibitors can be used to raise cAMP levels and prevent neurons from undergoing apoptosis. PDE4 inhibitors are also known to be anti-inflammatory. The combination of anti-apoptotic and anti-inflammatory properties make these compounds useful to treat neurodegeneration resulting from any disease or injury, including stroke, spinal cord injury, neurogenesis, Alzheimer's disease, multiple sclerosis, amylolaterosclerosis (ALS), and multiple systems atrophy (MSA).

Thus, in accordance with a preferred embodiment, the present invention includes methods of treating patients suffering from memory impairment due to, for example, Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia and other neurological conditions including acute neuronal diseases, as well as HIV and cardiovascular diseases, comprising administering an effective amount of a compound according to Formula I or II or pharmaceutically acceptable salts thereof.

The compounds of the present invention can also be used in a method of treating patients suffering from disease states characterized by decreased NMDA function, such as schizophrenia. The compounds can also be used to treat psychosis characterized by elevated levels of PDE 4, for example, various forms of depression, such as manic depression, major depression, and depression associated with psychiatric and neurological disorders.

As mentioned, the compounds of the invention also exhibit anti-inflammatory activity. As a result, the inventive compounds are useful in the treatment of a variety of allergic and inflammatory diseases, particularly disease states characterized by decreased cyclic AMP levels and/or elevated phosphodiesterase 4 levels. Thus, in accordance with a further embodiment of the invention, there is provided a method of treating allergic and inflammatory disease states, comprising administering an effective amount of a compound according to Formulas I or II or a pharmaceutically acceptable salt thereof. Such disease states include: asthma, chronic bronchitis, chronic obstructive pulmonary disease (COPD), atopic dermatitis, urticaria, allergic rhinitis, allergic conjunctivitis, vernal conjunctivitis, esoniophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, adult respiratory distress syndrome, cystic fibrosis, arterial restenosis, artherosclerosis, keratosis, rheumatoid spondylitis, osteoarthritis, pyresis, diabetes mellitus, pneumoconiosis, chronic obstructive airways disease, chronic obstructive pulmonary disease, toxic and allergic contact eczema, atopic eczema, seborrheic eczema, lichen simplex, sunburn, pruritis in the anogenital area, alopecia areata, hypertrophic scars, discoid lupus erythematosus, systemic lupus erythematosus, follicular and wide-area pyodermias, endogenous and exogenous acne, acne rosacea, Behcet's disease, anaphylactoid purpura nephritis, inflammatory bowel disease, leukemia, multiple sclerosis, gastrointestinal diseases, autoimmune diseases and the like.

PDE4 inhibitors for treating asthma, chronic bronchitis, psoriasis, allergic rhinitis, and other inflammatory diseases, and for inhibiting tumor necrosis factor are known within the art. See, e.g., WO 98/58901, JP-11-18957, JP 10-072415, WO 93/25517, WO 94/14742, U.S. Pat. No. 5,814,651, and U.S. Pat. No. 5,935,9778. These references also describe assays for determining PDE4 inhibition activity, and methods for synthesizing such compounds. The entire disclosures of these documents are hereby incorporated by reference.

PDE4 inhibitors may be used to prevent or ameliorate osteoporosis, as an antibiotic, for treatment of cardiovascular disease by mobilizing cholesterol from atherosclerotic lesions, to treat rheumatoid arthritis (RA), for long-term inhibition of mesenchymal-cell proliferation after transplantation, for treatment of urinary obstruction secondary to benign prostatic hyperplasia, for suppression of chemotaxis and reduction of invasion of colon cancer cells, for treatment of B cell chronic lymphocytic leukemia (B-CLL), for inhibition of uterine contractions, to attenuate pulmonary vascular ischemia-reperfusion injury (IRI), for corneal hydration, for inhibition of IL-2R expression and thereby abolishing HIV-1 DNA nuclear import into memory T cells, for augmentation of glucose-induced insulin secretion, in both the prevention and treatment of colitis, and to inhibit mast cell degranulation.

The compounds of the present invention can be administered as the sole active agent or in combination with other pharmaceutical agents such as other agents used in the treatment of cognitive impairment and/or in the treatment of psychosis, e.g., other PDE4 inhibitors, calcium channel blockers, chloinergic drugs, adenosine receptor modulators, amphakines NMDA-R modulators, mGluR modulators, and cholinesterase inhibitors (e.g., donepezil, rivastigimine, and glanthanamine). In such combinations, each active ingredient can be administered either in accordance with their usual dosage range or a dose below their usual dosage range.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention are typically administered at dosage levels and in a mammal customary for PDE4 inhibitors such as those known compounds mentioned above. For example, the compounds can be administered, in single or multiple doses, by oral administration at a dosage level of, for example, 0.01–100 mg/kg/day, preferably 0.1–70 mg/kg/day, especially 0.5–10 mg/kg/day. Unit dosage forms can contain, for example, 0.1–50 mg of active compound. For intravenous administration, the compounds can be administered, in single or multiple dosages, at a dosage level of, for example, 0.001–50 mg/kg/day, preferably 0.001–10 mg/kg/day, especially 0.01–1 mg/kg/day. Unit dosage forms can contain, for example, 0.1–10 mg of active compound.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The entire disclosures of all applications, patents and publications, cited above and below, and of U.S. Provisional Application No. 60/396,726, filed Jul. 19, 2002, are hereby incorporated by reference.

EXAMPLES

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

Example 1

6-Amino-1-cyclopentyl-3-ethyl-1H-indazole

To a mixture of 1-cyclopentyl-3-ethyl-1H-indazole-6-carboxylic acid (258 mg) and triethylamine (0.56 mL) in t-butanol (1 ml) was added diphenylphosphoryl azide (0.33 µL). The mixture was stirred at 100° C. for 4 h, then partitioned between water (25 mL) and ether (25 mL). The ether layer was collected, dried (MgSO$_4$), and passed through a plug of silica. The silica was washed with an additional 25 mL of ether and the mixture was concentrated in vacuo. The residue was dissolved in THF (5 mL) and 6N aq. HCL (1 mL) was added and the mixture was stirred for 18 h. Ether (25 mL) and water (25 mL) were added and the ether layer was collected, dried (MgSO$_4$), and concentrated in vacuo. The residue was purified by column chromatography on silica gel to yield 0.14 g of 6-amino-1-cyclopentyl-3-ethyl-1H-indazole (59% yield). $^1$H NMR (300 MHz) δ 7.45 (d,J=8.4 Hz, 1H), 6.52 (m,2H), 4.74 (p,J=7.8 Hz, 1H), 3.86 (br,2H), 2.95 (q,J=7.7 Hz,2H), 2.3–1.8 (m,6H), 1.8–1.6 (m,2H), 1.37 (t,J=7.7 Hz,3H).

Example 2

1-Cyclopentyl-3-ethyl-6-[N-(3-pyridylmethyl)]amino-1H-indazole

To a mixture of 3-pyridinecarboxaldehyde (106 mg, 1.0 mol) in methanol (5.0 mL) was added 6-amino-1-cyclopentyl-3-ethyl-1H-indazole (240 mg, 1.05 mmol) and p-toluenesulfonic acid monohydrate (2.0 mg). The reaction mixture was stirred for 4 h. The flask was then cooled to 0° C. and sodium borohydride (0.09 g, 2.3 mmol) was added portion-wise over 4 h. The reaction mixture was allowed to warm to room temperature over 16h with stirring. TLC indicated the reaction was complete (1:3 hex:EA). The solvent was evaporated and diluted with water (10 mL) and extracted with ethyl acetate (2×20 mL). The combined organic layers were washed with brine (5 mL), dried over sodium sulfate, and concentrated to yield the desired product. $^1$H NMR (300 MHz) δ 8.64 (s,1H), 8.51 (m,1H), 7.70 (m, 1H), 7.42 (d, J=8.4 Hz, 1H), 7.25 (m, 1H), 6.50 (m,1H), 6.33 (s,1H), 4.68 (p,J=7.8 Hz, 1H), 4.55 (br,1H), 4.40 (s,1H), 2.90 (q,J=7.7 Hz,2H), 2.1–1.8 (m,6H), 1.8–1.6 (m,2H), 1.34 (t,J=7.7 Hz,3H).

The following compounds were prepared in a similar manner as described above in Example 2.
1-Cyclopentyl-6-(3-pyridylmethyl)aminoindazole,
7-Methoxy-2-(2-methyl-(1,3-dioxolane-2-yl))-4-[N-(3-pyridylmethyl)]aminobenzofuran, and
7-Methoxy-2-(2-methyl-(1,3-dioxolane-2-yl))-4-[N-(4-pyridylmethyl)]aminobenzofuran.

Example 3

6-Amino-1-cyclopentyl-3-ethyl-6-[N-3-(1,1-dimethylethoxycarbonyl)phenyl]-N-(3-pyridylmethyl)amino-1H-indazole To a 10 mL oven dried, argon flushed flask was added in the following order 0.06 g (0.61 mmol) of NaOtBu, 36 mg of Pd$_2$ dba$_3$, 2.0 mL of toluene, 0.014 mL of P(tBu)$_3$, and a 2.0 mL solution of 140 mg (0.436 mmol) of 6-amino-1-cyclopentyl-3-ethyl-N-(3-pyridylmethyl)-1H-indazole in toluene. With stirring, 310 mg (1.5 mmol) of tert-butyl 3-iodobenzoate was added dropwise and the mixture was stirred for 18 hours. The reaction mixture was diluted with EtOAc and washed twice with H$_2$O and extracted with 3×15 mL of 3N HCl. The combined acid extracts were washed with 15 mL of EtOAc and then carefully neutralized with 6N NaOH to pH greater than 12. The basic solution was extracted with 2×15 mL of EtOAc and the combined organic fractions were subsequently washed with 15 mL of H$_2$O and brine, dried (MgSO$_4$), and concentrated. The residue was purified by chromatography over silica gel (Biotage Flash 40M) eluting with 25% EtOAc in hexanes. $^1$H NMR (300 MHz) δ 8.65 (br, 1H), 8.51 (br,1H), 8.26 (d, J=8.4, 1H), 7.75 (m, 1H), 7.7–7.5 (m, 3H), 7.27 (m, 1H), 7.1–7.0 (m, 2H), 6.85 (d, J=8.4,1H), 5.22 (s,1H), 4.76 (p,J=7.8 Hz, 1H), 2.96 (q,J=7.7 Hz,2H), 2.1–1.8 (m,6H), 1.8–1.6 (m,2H), 1.54 (s,9H), 1.34 (t,J=7.7 Hz,3H).

The following compounds were prepared in a similar manner as described above in Example 3.
7-Methoxy-2-(2-methyl-(1,3-dioxolane-2-yl))-4-[N-phenyl-N-(4-pyridylmethyl)]aminobenzofuran,
7-Methoxy-2-(2-methyl-(1,3-dioxolane-2-yl))-4-[N-(4-cyanophenyl)-N-(3-pyridylmethyl)]aminobenzofuran,
7-Methoxy-2-(2-methyl-(1,3-dioxolane-2-yl))-4-[N-(3-cyanophenyl)-N-(3-pyridylmethyl)]aminobenzofuran,
7-Methoxy-2-(2-methyl-(1,3-dioxolane-2-yl))-4-[N-phenyl-N-(3-pyridylmethyl)]aminobenzofuran,
7-Methoxy-2-(2-methyl-(1,3-dioxolane-2-yl))-4-[N-(3-cyanophenyl)-N-(4-pyridylmethyl)]aminobenzofuran,
7-Methoxy-2-(2-methyl-(1,3-dioxolane-2-yl))-4-[N-(4-acetylphenyl)-N-(3-pyridylmethyl)]aminobenzofuran,
7-Methoxy-2-(2-methyl-(1,3-dioxolane-2-yl))-4-[N-(4-carboxyphenyl)-N-(3-pyridylmethyl)]aminobenzofuran,
7-Methoxy-2-(2-methyl-(1,3-dioxolane-2-yl))-4-[N-(4-(2H-tetrazol-5-yl)phenyl)-N-(3-pyridylmethyl)]aminobenzofuran,
7-Methoxy-2-(2-methyl-(1,3-dioxolane-2-yl))-4-[N-(4-carboxy-3-chlorophenyl)-N-(3-pyridylmethyl)]aminobenzofuran,
7-Methoxy-2-(2-methyl-(1,3-dioxolane-2-yl))-4-[N-(3-carboxy-5-fluorophenyl)-N-(3-pyridylmethyl)]aminobenzofuran, 1-Cyclopentyl-6-[N-phenyl-N-(3-pyridylmethyl)]aminoindazole, and 1-Cyclopentyl-6-[N-(3-(1,1-dimethylethoxycarbonyl)phenyl)-N-(3-pyridylmethyl)]-1 H-aminoindazole.

Example 4

6-Amino-1-Cyclopentyl-3-ethyl-6-[N-(3-carboxyphenyl)-N-(3-pyridylmethyl)amino-1H-indazole A solution consisting of 170 mg (0.344 mmol) of 6-amino-1-cyclopentyl-3-ethyl-N-[3-(1,1-dimethylethoxycarbonyl)phenyl]-N-(3-pyridylmethyl)-1H-indazole, 3.35 mL of dichloromethane and 0.84 mL of trifluoroacetic acid was stirred at room temperature for 5 hours. The solution was washed with 5.0 mL of $H_2O$. Then 5.0 mL of $H_2O$ was added and the pH adjusted to 6 by the addition of 10% aqueous NaOH. The combined aqueous layers were extracted with 2×5 mL of dichloromethane. The combined dichloromethane extracts were evaporated and the remaining material was purified by flash chromatography over $SiO_2$ using 10% MeOH in $CH_2Cl_2$ as eluant. $^1$H NMR (300 MHz) δ 8.90 (br, 1H), 8.70 (br,1H), 8.25 (d, J=8.4, 1H), 7.7–7.5 (m, 4H), 7.20 (m, 1H), 7.1–7.0 (m, 2H), 6.86 (d, J=8.4,1H), 5.20 (s,1H), 4.76 (p,J=7.8 Hz, 1H), 2.96 (q,J=7.7 Hz,2H), 2.05 (m,4H), 1.88 (m,2H), 1.65 (m,2H), 1.36 (t,J=7.7 Hz,3H).

The following compound was prepared in a similar manner as described above in Example 4.

1-Cyclopentyl-6-[N-(3-carboxyphenyl)-N-(3-pyridylmethyl)]aminoindazole.

Example 5

2-Acetyl-7-methoxy-4-nitrobenzofuran

To a solution of 2-acetyl-7-methoxybenzofuran (4.0 g) in acetic anhydride (50 mL) at 0° C. was added 70% nitric acid (1.5 mL) drop-wise. The mixture was warmed to room temperature and stirred for 3 h then poured into ice-cold saturated sodium carbonate (200 mL). Solid sodium carbonate was added carefully with stirring until basic (pH=8). The mixture was filtered and the solid collected by vacuum filtration. The solid was boiled in 100 mL (methanol) for 1 h, then cooled to 0° C. and filtered to give 2-acetyl-7-methoxy-4-nitrobenzpfuran (2.1 g). $^1$H NMR (300 MHz) δ 8.29 (d,J=8.9 Hz, 1H), 8.14 (s,1H), 7.00 (d,J=8.9 Hz, 1H), 4.14 (s,3H), 2.68 (s, 3H).

Example 6

7-Methoxy-2-(2-methyl-(1,3-dioxolan-2-yl))-4-nitrobenzofuran

A mixture of 2-acetyl-7-methoxy-4-nitrobenzofuran (2.1 g), ethylene glycol (2 mL), and p-toluensulfonic acid (25 mg) in toluene (50 mL) was warmed to reflux with an attached Dean-Stark apparatus for 18 h. The mixture partitioned between sat. aq. $NaHCO_3$ (50 mL) and ether (50 mL). The ether layer was collected, washed with water (25 mL) and brine (25 mL), dried ($MgSO_4$) and concentrated to give pure 7-methozy-2-(2-methyl-(1,3-dioxolan-2-yl))-4-nitrobenzofuran (2.1 g). $^1$H NMR (300 MHz) δ 8.22 (d,J=9.0 Hz, 1H), 7.44 (s,1H), 6.84 (d,J=9.0 Hz, 1H), 4.11 (s,3H), 4.11 (m,4H), 1.86 (s,3H).

Example 7

4-Amino-7-metloxy-2-(2-methyl-(1,3-dioxolan-2-yl))-benzofuran

To a suspension of 10% Pd on activated carbon (200 mg) in ethanol (100 mL), under $N_2$ protection, was added 7-methoxy-2-(2-methyl-(1,3-dioxolan-2-yl))-4-nitrobenzofuran (6.50 g, 23 mmol). The reaction mixture was degassed under vacuum three times. The reaction mixture was stirred vigorously while hydrogen gas was allowed to flow over the reaction mixture. After 4 h the reaction was complete by TLC (5:1 hex:EA). The reaction mixture was filtered through a pad of celite and the celite was rinsed with additional ethanol. The solvent was removed in-vacuo to obtain 5.1 g (88% yield) of the title compound as a yellow oil.

Example 8

2-Acetyl-7-methoxy-4-(N-(3-carboxyphenyl)-N-(3-pyridylmethyl)aminobenzofuran

7-Methoxy-2-(2-methyl-1,3-dioxolan-2-yl)-4-(N-3-carboxyphenyl)-N-(3-pyridylmethyl)aminobenzofuran, t-butyl ester (120 mg) was taken up in $CH_2Cl_2$ (10 mL) and trifluoroacetic acid (2 mL) was added and the mixture was stirred for 4 h. The mixture was concentrated in vacuo and the residue was purified by column chromatography eluting with a linear gradient from 0%–10% MeOH in EtOAc over 15 min to yield 65 mg of 2-acetyl-7-methoxy-4-(N-(3-carboxyphenyl)-N-)3 pyridylmethyl)aminobenzofuran. $^1$H NMR (300 MHz) □ 11.60 (br,1H,) 8.71 (br,1H), 8.56 (br,1H), 7.80 (d,J=7.5 Hz, 1H), 7.60–7>50 (m,2H), 7.35 (m,1H), 7.20 (t,J=7.9 Hz, 1H), 7.10–7.00 (m,2H), 6.95–6.80 (m,2H), 5.09 (s,2H), 4.01 (s,3H), 2.54 (s,3H).

The following compounds were prepared in a similar manner as described above in Example 8.

2-Acetyl-7-methoxy-4-[N-phenyl-N-(4-pyridylmethyl)]aminobenzofuran,

2-Acetyl-7-methoxy-4-[N-(4-cyanophenyl)-N-(3-pyridylmethyl)]aminobenzofuran,

2-Acetyl-7-methoxy-4-[N-(3-cyanophenyl)-N-(3-pyridylmethyl)]aminobenzofuran,

2-Acetyl-7-methoxy-4-[N-phenyl-N-(3-pyridylmethyl)]aminobenzofuran,

2-Acetyl-7-methoxy-4-[N-(3-cyanophenyl)-N-(4-pyridylmethyl)]aminobenzofuran,

2-Acetyl-7-methoxy-4-[N-(4-acetylphenyl)-N-(3-pyridylmethyl)]aminobenzofuran,

2-Acetyl-7-methoxy-4-[N-(4-carboxyphenyl)-N-(3-pyridylmethyl)]aminobenzofuran,

2-Acetyl-7-methoxy-4-[N-(4-(2H-tetrazol-5-yl)phenyl)-N-(3-pyridylmethyl]aminobenzofuran, 2-Acetyl-7-methoxy-4-[N-(4-carboxy-3-chlorophenyl)-N-(3-pyridylmethyl)]aminobenzofuran, and 2-Acetyl-7-methoxy-4-[N-(3-carboxy-5-fluorophenyl)-N-(3-pyridylmethyl)]aminobenzofuran.

Example 9

2-Acetyl-7-methoxy-N-(4-phenylsulfonylaminocarbonylphenyl)-N-(3-pyridylmethyl)-4-aminobenzofuran To a solution of 2-acetyl-7-methoxy-N-(4-carboxyphenyl)-N-(3-pyridylmethyl)-4-aminobenzofuran (416 mg, 1.0 mmol), benzenesulfonamide (200 mg, 1.2 mmol), and DMAP (150 mg, 1.2 mmol) in dichloromethane (5 mL) at room temperature was added EDCI (230 mg, 1.2 mmol) in one portion and the mixture was stirred at room temperature for 16 h. The mixture was partitioned between water (25 mL) and EtOAc (25 mL) and the pH was adjusted to 5–6 with 1.0N HCl. The EtOAc was separated, washed with brine (25 mL), dried (MgSO$_4$) and concentrated in vacuo. The residue was purified by column chromatography eluting with a linear gradient from 5% to 10% MeOH in EtOAc to give 2-Acetyl-7-methoxy-N-(4-phenylsulfonylaminocarbonylphenyl)-N-(3-pyridylmethyl)-4-aminobenzofuran (415 mg). $^1$H NMR (300 MHz) δ 8.53 (br,1H), 8.46 (br,1H), 8.06 (d,J=7.3 Hz,2H), 7.8–7.3 (m,6H), 7.21 (m,1H), 7.1–7.0 (m,2H), 6.91 (d,J=8.5 Hz,1H), 6.56 (d,J=7.3 Hz,2H), 4.99 (s,2H), 4.02 (s,3H), 2.54 (s,3H).

Example 10

In Vitro Measurement of Type 4 Phosphodiesterase Inhibition Activity

Human PDE4 was obtained from baculovirus-infected Sf9 cells that expressed the recombinant enzyme. The cDNA encoding hPDE-4D6 was subcloned into a baculovirus vector. Insect cells (Sf9) were infected with the baculovirus and cells were cultured until protein was expressed. The baculovirus-infected cells were lysed and the lysate was used as source of hPDE-4D6 enzyme. The enzyme was partially purified using a DEAE ion exchange chromatography. This procedure can be repeated using cDNA encoding other PDE-4 enzymes.

Assay:

Type 4 phosphodiesterases convert cyclic adenosine monophosphate (cAMP) to 5'-adenosine monophosphate (5'-AMP). Nucleotidase converts 5'-AMP to adenosine. Therefore the combined activity of PDE4 and nucleotidase converts cAMP to adenosine. Adenosine is readily separated from cAMP by neutral alumina columns. Phosphodiesterase inhibitors block the conversion of cAMP to adenosine in this assay; consequently, PDE4 inhibitors cause a decrease in adenosine.

Cell lysates (40 ul) expressing hPDE-4D6 were combined with 50 ul of assay mix and 10 ul of inhibitors and incubated for 12 min at room temperature. Final concentrations of assay components were: 0.4 ug enzyme, 10 mM Tris-HCl (pH 7.5), 10 MM MgCl$_2$, 3 uM cAMP, 0.002 U 5'-nucleotidase, and 3×10$^4$ cpm of [3H]cAMP. The reaction was stopped by adding 100 μl of boiling 5 mN HCl. An aliquot of 75 μl of reaction mixture was transferred from each well to alumina columns (Multiplate; Millipore). Labeled adenosine was eluted into an OptiPlate by spinning at 2000 rpm for 2 min; 150 μl per well of scintillation fluid was added to the OptiPlate. The plate was sealed, shaken for about 30 min, and cpm of [$^3$H]adenosine was determined using a Wallac Triflux®.

All test compounds are dissolved in 100% DMSO and diluted into the assay such that the final concentration of DMSO is 0.1%. DMSO does not affect enzyme activity at this concentration.

A decrease in adenosine concentration is indicative of inhibition of PDE activity. pIC$_{50}$ values were determined by screening 6 to 12 concentrations of compound ranging from 0.1 nM to 10,000 nM and then plotting drug concentration versus $^3$H-adenosine concentration. Nonlinear regression software (Assay Explorer®) was used to estimate pIC$_{50}$ values.

Example 11 (Method A)

Passive Avoidance in Rats, an in Vivo Test for Learning and Memory

The test was performed as previously described (Zhang, H.-T., Crissman, A. M., Dorairaj, N. R., Chandler, L. J., and O'Donnell, J. M., *Neuropsychopharmacology*, 2000, 23, 198–204.). The apparatus (Model E10-16SC, Coulboum Instruments, Allentown, Pa.) consisted of a two-compartment chamber with an illuminated compartment connected to a darkened compartment by a guillotine door. The floor of the darkened compartment consisted of stainless steel rods through which an electric foot-shock could be delivered from a constant current source. All experimental groups were first habituated to the apparatus the day before the start of the experiment. During the training, the rat (Male Spraque-Dawley (Harlan) weighing 250 to 350 g) was placed in the illuminated compartment facing away from the closed guillotine door for 1 minute before the door was raised. The latency for entering the darkened compartment was recorded. After the rat entered the darkened compartment, the door was closed and a 0.5 mA electric shock was administered for 3 seconds. Twenty-four hours later, the rat was administered 0.1 mg/kg MK-801 or saline, 30 minutes prior to the injection of saline or test compound (dosed from 0.1 to 2.5 mg/kg, i.p.), which was 30 minutes before the retention test started. The rat was again placed in the illuminated compartment with the guillotine door open. The latency for entering the darkened compartment was recorded for up to 180 seconds, at which time the trial was terminated.

All data were analyzed by analyses of variance (ANOVA); individual comparisons were made using Kewman-Keuls tests. Naïve rats required less than 30 seconds, on average, to cross from the illuminated compartment to the darkened compartment. However, 24 hours after the electric shock exposure, most rats pretreated with vehicle did not re-enter the darkened compartment; the average latency was increased up to 175 seconds (p<0.001). Pretreatment with MK-801 (0.1 mg/kg) markedly reduced this latency when compared to the vehicle (p<0.001). This amnesic effect of MK-801 is reversed in a statistically significant manner by actual test compounds in a dose-dependent fashion.

Example 11 (Method B)

Radial Arm Maze Task in Rats, an in Vivo Test for Learning and Memory

The test was performed as previously described (Zhang, H.-T., Crissman, A. M., Dorairaj, N. R., Chandler, L. J., and O'Donnell, J. M., *Neuropsychopharmacology*, 2000, 23, 198–204.). Five days after initial housing, rats (male Spraque-Dawley (Harlan) weighing 250 to 350 g) were placed in the eight-arm radial maze (each arm was 60×10× 12 cm high; the maze was elevated 70 cm above the floor) for acclimation for two days. Rats were then placed individually in the center of the maze for 5 minutes with food pellets placed close to the food wells, and then, the next day, in the wells at the end of the arms; 2 sessions a day were conducted. Next, four randomly selected arms were then baited with one pellet of food each. The rat was restricted to the center platform (26 cm in diameter) for 15 seconds and then allowed to move freely throughout the maze until it collected all pellets of food or 10 minutes passed, whichever came first. Four parameters were recorded: 1) working memory errors, i.e., entries into baited arms that had already been visited during the same trial; 2) reference memory errors, i.e., entries into unbaited arms; 3) total arm entries; and 4) the test duration (seconds), i.e., the time spent in the collection of all the pellets in the maze. If the working memory error was zero and the average reference memory error was less than one in five successive trials, the rats began the drug tests. MK-801 or saline was injected 15 minutes prior to vehicle or test agent, which was given 45 minutes before the test. Experiments were performed in a lighted room, which contained several extra-maze visual cues.

All data were analyzed by analyses of variance (ANOVA); individual comparisons were made using Kewman-Keuls tests. Compared to control, MK-801 (0.1 mg/kg, i.p.) increased the frequencies of both working and reference memory errors (p<0.01). This amnesic effect of MK-801 on working memory is reversed in a statistically significant manner by the administration of actual test compounds in a dose-dependent fashion.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention.

We claim:

1. A compound of the formula II:

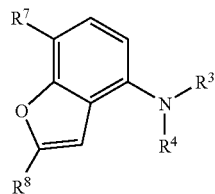

wherein
$R^3$ is H,
alkyl having 1 to 8 carbon atoms, which is branched or unbranched and which is unsubstituted or substituted one or more times with halogen, cyano, $C_{1-4}$-alkoxy, or combinations thereof,
a partially unsaturated carbocycle-alkyl group wherein the carbocyclic portion has 5 to 14 carbon atoms and the alkyl portion which is branched or unbranched has 1 to 5 carbon atoms, and which is unsubstituted or substituted in the carbocyclic portion one or more times by halogen, alkyl, alkoxy, nitro, cyano, oxo, or combinations thereof, and the ailcyl portion is optionally substituted by halogen, $C_{1-4}$-alkoxy, cyano or combinations thereof, arylalkyl having 7 to 19 carbon atoms, wherein the aryl portion has 6 to 14 carbon atoms and the alkyl portion, which is branched or unbranched, has 1 to 5 carbon atoms, arylalkyl radical is unsubstituted or substituted, in the aryl portion, one or more times by halogen, trifluoromethyl, $CF_3O$, nitro, amino, alkyl, alkoxy, alkylamino, dialkylamino and/or substituted in the alkyl portion by halogen, cyano, or methyl, or
heterocycle-alkyl group, wherein the heterocyclic portion may be aromatic, or partially or fully saturated
and has 5 to 10 ring atoms in which at least 1 ring atom is a N, O or S atom, the alkyl portion, which is branched or unbranched, has 1 to 5 carbon atoms, the heterocycle-alkyl group is unsubstituted or substituted one or more times in the heterocyclic portion by halogen, alkyl, alkoxy, cyano, trifluoromethyl, $CF_3O$, nitro, oxo, amino, alkylamino, dialkylamino, or combinations thereof and/or substituted in the alkyl portion by halogen, cyano, or methyl or combinations thereof;

$R^4$ is H,
aryl having 6 to 14 carbon atoms and which is unsubstituted or substituted one or more times by halogen, alkyl, alkenyl, alkynyl, hydroxy, alkoxy, alkoxyalkoxy, nitro, methylenedioxy, ethylenedioxy, trifluoromethyl, $OCF_3$, amino, aminoalkyl, aminoalkoxy dialkylamino, hydroxyalkyl, hydroxamic acid, tetrazole-5-yl, 2(-heterocycle)tetrazole-5-yl, hydroxyalkoxy, carboxy, alkoxycarbonyl, cyano, acyl, alkylthio, alkylsulfinyl, alkylsulfonyl, phenoxy, trialkylsilyloxy, $R^5$-L-, or combinations thereof, or
heteroaryl having 5 to 10 ring atoms in which at least 1 ring atom is a heteroatom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, trialkylsilyloxy, $R^5$-L-, or combinations thereof;

$R^5$ is H,
alkyl having 1 to 8 carbon atoms, which is unsubstituted or substituted one or more times with halogen, $C_{1-4}$-alkyl, $C_{1-4}$-alkoxy, oxo, or combinations thereof,
alkylamino or dialkylamino wherein each alkyl portion has independently 1 to 8 carbon atoms,
a partially unsaturated carbocycle-alkyl group wherein the carbocyclic portion has 5 to 14 carbon atoms and the alkyl portion has 1 to 5 carbon atoms, which is unsubstituted or substituted, preferably in the carbocyclic portion, one or more times by halogen, alkyl, alkoxy, nitro, cyano, oxo, or combinations thereof
cycloalkyl having 3 to 10 carbon atoms, which is unsubstituted or substituted one or more times by halogen, hydroxy, oxo, cyano, alkoxy, alkyl having 1 to 4 carbon atoms, or combinations thereof,
cycloalkylalkyl having 4 to 16 carbon atoms, which is unsubstituted or substituted in the cycloalkyl portion and/or the alkyl portion one or more times by halogen, oxo, cyano, hydroxy, alkyl, alkoxy or combinations thereof,
aryl having 6 to 14 carbon atoms and which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl,
arylalkyl having 7 to 19 carbon atoms, wherein the aryl portion has 6 to 14 carbon atoms and the alkyl portion, which is branched or unbranched, has 1 to 5 carbon atoms, arylalkyl radical is unsubstituted or substituted, in the aryl portion, one or more times by halogen, trifluoromethyl, CF₃O, nitro, amino, alkyl, alkoxy, amino, alkylamino, dialkylamino and/or substituted in the alkyl portion by halogen, cyano, or methyl, a heterocyclic group, which is saturated, partially saturated or unsaturated, having 5 to 10 ring atoms in which at least 1 ring atom is a N, O or S atom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, or combinations thereof, or a heterocycle-alkyl group, wherein the heterocyclic portion is saturated, partially saturated or unsaturated, and has 5 to 10 ring atoms in which at least 1 ring atom is a N, 0 or S atom, and the alkyl portion which is branched or unbranched and has 1 to 5 carbon atoms, the heterocycle-alkyl group is unsubstituted or substituted one or more times in the heterocyclic portion by halogen, alkyl, alkoxy, cyano, trifluoromethyl, CF₃O, nitro, oxo, amino, alkylamino, dialkylamino, or combinations thereof and/or substituted in the alkyl portion by halogen, cyano, or methyl or combinations thereof;

L is a single bond or a divalent aliphatic radical having up to 8 carbon atoms wherein one or more —CH₂— groups are each optionally replaced by —O—, —S—, —SO₂—, —SO—, —NR⁶—, —SO₂NH—, —NHSO₂—, —CO—, —NR₆CO—, —CONR⁶—, —NHCONH—, —OCONH—, —NHCOO—, —SCONH—, —SCSNH—, or —NHCSNH—;

R⁶ is H,
alkyl having 1 to 8 carbon atoms, which is branched or unbranched and which is unsubstituted or substituted one or more times with halogen, C₁₋₄-alkyl, C₁₋₄-alkoxy, oxo, or combinations thereof;

R⁷ is alkoxy or alkylthio, in each case having 1 to 4 carbon atoms, which is branched or unbranched and which is unsubstituted or substituted one or more times by halogen;

R⁸ is —CO—C₁₋₄-alkyl which is branched or unbranched and where the alkyl is unsubstituted or substituted one or more times by halogen, or is

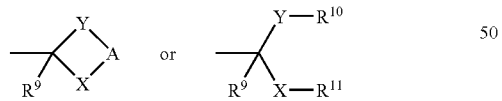

R⁹ is H or alkyl having 1 to 4 carbon atoms, which is branched or unbranched, and which is unsubstituted or substituted one or more times by halogen;

R¹⁰ is alkyl having 1 to 6 carbon atoms, which is branched or unbranched, and which is unsubstituted or substituted one or more times by halogen;

R¹¹ is alkyl having 1 to 6 carbon atoms, which is branched or unbranched, and which is unsubstituted or substituted one or more times by halogen;

X and Y are each independently 0 or S; and

A is alkylene having 2 to 7 carbon atoms which is unsubstituted or substituted one or more times by halogen;

wherein at least one of R³ and R⁴ is other than H; or
a pharmaceutically acceptable salt thereof;
wherein an optically active compound can be in the form of one of its separate enantiomers or mixtures thereof, including racemic mixtures.

2. A compound of claim 1, which is of formula III or IV:

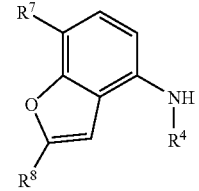

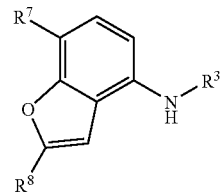

wherein
R³ is alkyl having 1 to 8 carbon atoms, which is branched or unbranched and which is unsubstituted or substituted one or more times with halogen, cyano, C₁₋₄-alkoxy, or combinations thereof, a partially unsaturated carbocycle-alkyl group wherein the carbocyclic portion has 5 to 14 carbon atoms and the alkyl portion which is branched or unbranched has 1 to 5 carbon atoms, and which is unsubstituted or substituted in the carbocyclic portion one or more times by halogen, alkyl, alkoxy, nitro, cyano, oxo, or combinations thereof, and the alkyl portion is optionally substituted by halogen, C₁₋₄-alkoxy, cyano or combinations thereof, arylalkyl having 7 to 19 carbon atoms, wherein the aryl portion has 6 to 14 carbon atoms and the alkyl portion, which is branched or unbranched, has 1 to 5 carbon atoms, arylalkyl radical is unsubstituted or substituted, in the aryl portion, one or more times by halogen, trifluoromethyl, CF₃O, nitro, amino, alkyl, alkoxy, alkylamino, dialkylamino and/or substituted in the alkyl portion by halogen, cyano, or methyl, or heterocycle-alkyl group, wherein the heterocycle portion may be partially or fully saturated and has 5 to 10 ring atoms in which at least 1 ring atom is a N, O or S atom, the alkyl portion, which is branched or unbranched, has 1 to 5 carbon atoms, the heterocycle-alkyl group is unsubstituted or substituted one or more times in the heterocycle portion by halogen, alkyl, alkoxy, cyano, trifluoromethyl, CF₃O, nitro, oxo, amino, alkylamino, dialkylamino, or combinations thereof and/or substituted in the alkyl portion by halogen, cyano, or methyl or combinations thereof;

R⁴ is aryl having 6 to 14 carbon atoms and which is unsubstituted or substituted one or more times by halogen, alkyl, alkenyl, alkynyl, hydroxy, alkoxy, alkoxyalkoxy, nitro, methylenedioxy, ethylenedioxy, trifluoromethyl, OCF₃, amino, aminoalkyl, aminoalkoxy dialkylamino, hydroxyalkyl, hydroxamic acid, tetrazole-5-yl, 2(-heterocycle)tetrazole-5-yl, hydroxyalkoxy, carboxy, alkoxycarbonyl, cyano, acyl, alkylthio, alkylsulfinyl, alkylsulfonyl, phenoxy, trialkylsilyloxy, $R^5$-L-, or combinations thereof, or heteroaryl having 5 to 10 ring atoms in which at least 1 ring atom is a heteroatom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, trialkylsilyloxy, $R^5$-L-, or combinations thereof;

$R^7$ is alkoxy or alkylthio, in each case having 1 to 4 carbon atoms, which is branched or unbranched and which is unsubstituted or substituted one or more times by halogen;

$R^8$ is —CO—$C_{1-4}$-alkyl which is branched or unbranched and where the alkyl is unsubstituted or substituted one or more times by halogen, or is

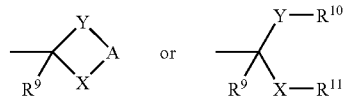

or a pharmaceutically acceptable salt thereof;

wherein an optically active compound can be in the form of one of its separate enantiomers or mixtures thereof, including racemic mixtures.

3. A compound of claim 1, which is of the subformula VI:

VI

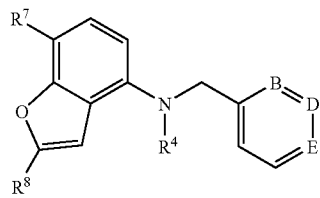

wherein $R^4$ is H, aryl having 6 to 14 carbon atoms and which is unsubstituted or substituted one or more times by halogen, alkyl, alkenyl, alkynyl, hydroxy, alkoxy, alkoxyalkoxy, nitro, methylenedioxy, ethylenedioxy, trifluoromethyl, $OCF_3$, amino, aminoalkyl, aminoalkoxy dialkylamino, hydroxyalkyl, hydroxamic acid, tetrazole-5-yl, 2(-heterocycle)tetrazole-5-yl, hydroxyalkoxy, carboxy, alkoxycarbonyl, cyano, acyl, alkylthio, alkylsulfinyl, alkylsulfonyl, phenoxy, trialkylsilyloxy, $R^5$-L-, or combinations thereof, or heteroaryl having 5 to 10 ring atoms in which at least 1 ring atom is a heteroatom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, phenoxy, trialkylsilyloxy, $R^5$-L-, or combinations thereof;

$R^7$ is alkoxy or alkylthio, in each case having 1 to 4 carbon atoms, which is branched or unbranched and which is unsubstituted or substituted one or more times by halogen;

$R^8$ is —CO—$C_{1-4}$-alkyl which is branched or unbranched and where the alkyl is unsubstituted or substituted one or more times by halogen, or is

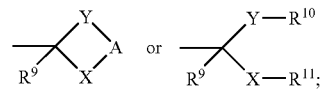

and one of B, D and E is N and the other two are C.

4. A compound of claim 3, wherein D is N and B and E are C.

5. A compound of claim 3, wherein $R^4$ is pyridyl or phenyl which are unsubstituted or substituted one or more times by halogen, alkyl, alkenyl, alkynyl, hydroxy, alkoxy, alkoxyalkoxy, nitro, methylenedioxy, ethylenedioxy, trifluoromethyl, $OCF_3$, amino, aminoalkyl, aminoalkoxy dialkylamino, hydroxyalkyl, hydroxamic acid, tetrazole-5-yl, 2(-heterocycle)tetrazole-5-yl, hydroxyalkoxy, carboxy, alkoxycarbonyl, cyano, acyl, alkylthio, alkylsulfinyl, alkylsulfonyl, phenoxy, trialkylsilyloxy, $R^5$-L-, or combinations thereof.

6. A compound of claim 1, which is:

7-Methoxy-2-(2-methyl-(1,3-dioxolane-2-yl))-4-[N-(4-pyridylmethyl)]aminobenzofuran, 7-Methoxy-2-(2-methyl-(1,3-dioxolane-2-yl))-4-[N-(3-pyridylmethyl)]aminobenzofuran, 7-Methoxy-2-(2-methyl-(1,3-dioxolane-2-yl))-4-[N-phenyl-N-(4-pyridylmethyl)]aminobenzofuran, 7-Methoxy-2-(2-methyl-(1,3-dioxolane-2-yl))-4-[N-(3-cyanophenyl)-N-(3-pyridylmethyl)]aminobenzofuran, 7-Methoxy-2-(2-methyl-(1,3-dioxolane-2-yl))-4-[N-phenyl-N-(3-pyridylmethyl)]aminobenzofuran, 7-Methoxy-2-(2-methyl-(1,3-dioxolane-2-yl))-4-[N-(3-cyanophenyl)-N-(4-pyridylmethyl)]aminobenzofuran, 7-Methoxy-2-(2-methyl-(1,3-dioxolane-2-yl))-4-[N-(4-acetylphenyl)-N-(3-pyridylmethyl)]aminobenzofuran, 7-Methoxy-2-(2-methyl-(1,3-dioxolane-2-yl))-4-[N-(4-carboxyphenyl)-N-(3-pyridylmethyl)]aminobenzofuran, 7-Methoxy-2-(2-methyl-(1,3-dioxolane-2-yl))-4-[N-(4-(2H-tetrazol-5-yl)phenyl)-N-(3pyridylmethyl]aminobenzofuran, 7-Methoxy-2-(2-methyl-(1,3-dioxolane-2-yl))-4-[N-(4-carboxy-3-chlorophenyl)-N-(3-pyridylmethyl)]aminobenzofuran, 7-Methoxy-2-(2-methyl-(1,3-dioxolane-2-yl))-4-[N-(3-carboxy-5-fluorophenyl)-N-(3-pyridylmethyl)]aminobenzofuran, 2-Acetyl-7-methoxy-4-(N-(4-cyanophenyl)-N-(3-pyridylmethyl))aminobenzofuran, 2-Acetyl-7-methoxy-4-(N-phenyl-N-(4-pyridylmethyl))aminobenzofuran, 2-Acetyl-7-methoxy-4-(N-(3-carboxyphenyl)-N-(3-pyridylmethyl))aminobenzofuran, 7-Methoxy-2-(2-methyl-(1,3-dioxolane-2-yl))-4-(N-(4-cyanophenyl)-N-(3-pyridylmethyl))-aminobenzofuran, 2-Acetyl-7-methoxy-4-(N-(3-cyanophenyl)-N-(3-pyridylmethyl))aminobenzofuran, 2-Acetyl-7-methoxy-4-(N-phenyl-N-(3-pyridylmethyl))aminobenzofuran, 2-Acetyl-7-methoxy-4-(N-(3-cyanophenyl)-N-(4-pyridylmethyl))aminobenzofuran,
2-Acetyl-7-methoxy-4-(N-(4-acetylphenyl)-N-(3-pyridylmethyl))aminobenzofuran,
2-Acetyl-7-methoxy-4-[N-(4-carboxyphenyl)-N-(3-pyridylmethyl)]aminobenzofuran,
2-Acetyl-7-methoxy-4-[N-(4-(2H-tetrazol-5-yl)phenyl)-N-(3-pyridylmethyl]aminobenzofuran,
2-Acetyl-7-methoxy-4-[N-(4-carboxy-3-chlorophenyl)-N-(3-pyridylmethyl)]aminobenzofuran,
2-Acetyl-7-methoxy-4-[N-(3-carboxy-5-fluorophenyl)-N-(3-pyridylmethyl)]aminobenzofuran,
2-Acetyl-7-methoxy-N-(4-phenylsulfonylaminocarbonylphenyl)-N-(3-pyridylmethyl]-4-aminobenzofuran, or
a pharmaceutically acceptable salt thereof,
wherein optically active compounds can be in the form of their separate enantiomers or mixtures thereof, including racemic mixtures.

7. A compound of claim 1, wherein:
each aryl group is, independently, a phenyl, naphthyl or biphenyl group optionally substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, or phenoxy;
each heteroaryl group is, independently, a furyl, thienyl, pyrrolyl, pyrazolyl, imidazolyl, triazolyl, tetrazolyl, dithialyl, oxathialyl, isoxazolyl, oxazolyl, thiazolyl, isothiazolyl, oxadiazolyl, oxatriazolyl, dioxazolyl, oxathiazolyl, thiadiazolyl, pyridyl, pyridazinyl, pyrimidinyl, pyrazinyl, triazinyl, oxazinyl, isoxazinyl, oxathiazinyl, oxadiazinyl, benzofuranyl, isobenzofuranyl, thionaphthenyl, isothionaphthenyl, indolyl, isoindolyl, indazolyl, benzisoxazolyl, benzoxazolyl, benzthiazolyl, benzisothiazolyl, purinyl, benzopyranyl, quinolinyl, isoquinolinyl, cinnolinyl, quinazolinyl, naphthyridinyl, or benzoxazinyl group optionally substituted in one or more places by halogen, aryl, alkyl, alkoxy, carboxy, methylene, cyano, trifluoromethyl, nitro, amino, alkylamino, or dialkylamino; and
each heterocycle group is, independently, a heteroaryl group as stated above or a tetrahydrofuranyl, piperidinyl, or pyrrolidinyl group optionally substituted as stated above.

8. A compound of claim 1, wherein:
$R^3$ is hydrogen; alkyl having 1 to 4 carbon atoms; substituted or unsubstituted benzyl, phenethyl, and phenpropyl; or substituted or unsubstituted pyridylmethyl, furanylmethyl, thienylmethyl, pyrrolylmethyl, pyrimidinylmethyl, thiazolylmethyl, isoquinolinylmethyl and quinolinylmethyl;
$R^4$ is phenyl, naphthyl, biphenyl, furanyl, pyrazinyl, pyrimidinyl, pyridyl, quinolinyl, and isoquinolinyl, which in each case is unsubstituted or is substituted one or more times by OH, F, Cl, $CF_3$, alkyl, alkoxy, CN, vinyl, $CH_2OH$, CONHOH, $CONH_2$, methylenedioxy or COOH, or when $R^4$ is phenyl, is optionally substituted by $R^5$—, $R^5$—O—, $R^5$—CO—, $R^5$—NH—CO—, $R^5$—$SO_2$—NH-alkylene-O—, $NH_2$-alkyl-NH—CO—, $R^5$-alkylene-NH—CO—, alkyl-CO—NH-alkyl- as well as methyl, ethyl, Cl, F, CN, $OCH_3$, $CF_3$, amino, nitro, $HOCH_2$ or COOH;
$R^7$ is alkoxy having 1 to 4 carbon atoms, which is branched or unbranched and which is unsubstituted or substituted one or more times by halogen; and
$R^8$ is —CO—$C_{1-4}$-alkyl.

9. A compound of claim 1, wherein:
$R^3$ is arylalkyl or heteroarylalkyl, in each case substituted or unsubstituted; and
$R^4$ is H or is aryl or heteroaryl, in each case substituted or unsubstituted.

10. A compound of claim 1, wherein:
$R^3$ is pyridylmethyl which is substituted or unsubstituted; and
$R^4$ is H or is aryl or heteroaryl, in each case substituted or unsubstituted.

11. A compound of claim 1, wherein:
$R^3$ is pyridylmethyl which is substituted or unsubstituted; and
$R^4$ is phenyl which is substituted or unsubstituted.

12. A compound of claim 1, wherein:
$R^7$ is alkoxy having 1 to 4 carbon atoms;
$R^8$ is COCH3 or

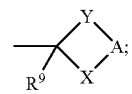

$R^9$ is —$CH_3$;
X and Y are both O or S; and
A is —$CH_2CH_2$—.

13. A compound of claim 1, wherein:
$R^3$ is arylalkyl or heteroarylalkyl, in each case substituted or unsubstituted; and
$R^4$ is H or is aryl or heteroaryl, in each case substituted or unsubstituted;
$R^7$ is alkoxy having 1 to 4 carbon atoms;
$R^8$ is $COCH_3$ or

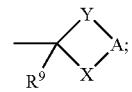

$R^9$ is —$CH_3$;
X and Y are both O or S; and
A is —$CH_2CH_2$—.

14. A compound of claim 1, wherein:
$R^3$ is pyridylmethyl which is substituted or unsubstituted;
$R^4$ is H or is aryl or heteroaryl, in each case substituted or unsubstituted;
$R^7$ is alkoxy having 1 to 4 carbon atoms;
$R^8$ $COCH_3$ or

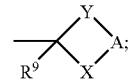

$R^9$ is —$CH_3$;
X and Y are both O or S; and
A is —$CH_2CH_2$—.

15. A compound of claim 1, wherein:
$R^3$ is pyridylmethyl which is substituted or unsubstituted;
$R^4$ is phenyl which is substituted or unsubstituted;
$R^7$ is alkoxy having 1 to 4 carbon atoms;
$R^8$ is $COCH_3$ or

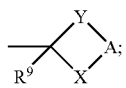

R⁹ is —CH₃;
X and Y are both O or S; and
A is —CH₂CH₂—.

16. A pharmaceutical composition containing a compound of claim 1 and a pharmaceutically acceptable carrier.

17. A composition of claim 16, wherein the compound of claim 1 is provided in a unit dosage of 0.1–50 mg.

18. A method for enhancing cognition in a patient comprising administering to said patient an effective amount of a compound according to claim 1.

19. A method according to claim 18, wherein said compound is administered in an amount of 0.01–100 mg/kg of body weight/day.

20. A method according to claim 18, wherein said patient is a human.

21. A method of claim 18, wherein the patient is suffering from cognition impairment or decline.

22. A method according to claim 18, wherein said patient is suffering from memory impairment.

23. A method according to claim 22, wherein said patient is suffering from memory impairment due to dementia.

24. A method of treating a patient suffering from inflammation comprising administering to said patient an effective amount of a compound according to claim 1.

25. A method according to claim 22, wherein said patient is suffering from memory impairment due to Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia, an acute neuronal disease, age-related cognitive decline, HIV or a cardiovascular disease.

26. A compound according to claim 1, wherein R³ is methyl, ethyl, propyl, isopropyl, butyl, sec-butyl, tert-butyl, pentyl, hexyl, heptyl, octyl, 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, or an alkyl having 1 to 8 carbon atoms, which is branched or unbranched and which is substituted one or more times with halogen.

27. A compound according to claim 1, wherein R⁴ is phenyl, naphthyl or biphenyl, which is unsubstituted or substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, or phenoxy, and acyl is an alkanoyl radical having 1 to 13 carbon atoms in which the alkyl portion is unsubstituted or substituted by halogen, alkyl, aryl and/or alkoxy, or acyl is an aroyl radical having 7 to 15 carbon atoms in which the aryl portion is unsubstituted or substituted by halogen, alkyl and/or alkoxy.

28. A compound according to claim 1, wherein R³ is benzyl, 1-phenethyl, 2-phenethyl, phenpropyl, phenbutyl, phenpentyl, or napthylmethyl.

29. A compound according to claim 1, wherein R⁴ is furyl, thienyl, pyrrolyl, pyrazolyl, imidazolyl, triazolyl, tetrazolyl, dithialyl, oxathialyl, isoxazolyl, oxazolyl, thiazolyl, isothiazolyl, oxadiazolyl, oxatriazolyl, dioxazolyl, oxathiazolyl, thiadiazolyl, pyridyl, pyridazinyl, pyrimidinyl, pyrazinyl, triazinyl, oxazinyl, isoxazinyl, oxathiazinyl, oxadiazinyl, benzofuranyl, isobenzofuranyl, thionaphthenyl, isothionaphthenyl, indolyl, isoindolyl, indazolyl, benzisoxazolyl, benzoxazolyl, benzthiazolyl, benzisothiazolyl, purinyl, benzopyranyl, quinolinyl, isoquinolinyl, cinnolinyl, quinazolinyl, naphthyridinyl, or benzoxazinyl, which in each case is unsubstituted or substituted in one or more places by halogen, aryl, alkyl, alkoxy, carboxy, methylene, cyano, trifluoromethyl, nitro, amino, alkylamino, or dialkylamino.

30. A compound according to claim 1, wherein R⁴ is 2-thienyl, 3-thienyl, 2-, 3- or 4-pyridyl, 2-, 3-, 4-, 5-, 6-, 7- or 8-quinolinyl, or 1-, 3-, 4-, 5-, 6-, 7- or 8-isoquinolinyl, which in each case is unsubstituted or substituted in one or more places by halogen, aryl, alkyl, alkoxy, carboxy, methylene, cyano, trifluoromethyl, nitro, amino, alkylamino, or dialkylamino.

31. A compound according to claim 1, wherein R³ is hydrogen, methyl, ethyl, n-propyl, n-butyl, benzyl, benzyl substituted by F, Cl, CH₃, C₂H₅, OCH₃, CN, or combinations thereof, phenethyl, phenethyl substituted by F, Cl, CH₃, C₂H₅, OCH₃, CN, or combinations thereof, phenpropyl, phenpropyl substituted by F, Cl, CH₃, C₂H₅, OCH₃, CN, or combinations thereof, pyridylmethyl, pyridylmethyl substituted by are F, Cl, CH₃, C₂H₅, OCH₃, CN, or combinations thereof, furanylmethyl, furanylmethyl substituted by are F, Cl, CH₃, C₂H₅, OCH₃, CN, or combinations thereof, thienylmethyl, thienylmethyl substituted by are F, Cl, CH₃, C₂H₅, OCH₃, CN, or combinations thereof, pyrrolylmethyl, pyrrolylmethyl substituted by are F, Cl, CH₃, C₂H₅, OCH₃, CN, or combinations thereof, pyrimidinylmethyl, pyrimidinylmethyl substituted by are F, Cl, CH₃, C₂H₅, OCH₃, CN, or combinations thereof, thiazolylmethyl, thiazolylmethyl substituted by are F, Cl, CH₃, C₂H₅, OCH₃, CN, or combinations thereof, isoquinolinylmethyl, isoquinolinylmethyl substituted by are F, Cl, CH₃, C₂H₅, OCH₃, CN, or combinations thereof, quinolinylmethyl, or quinolinylmethyl substituted by are F, Cl, CH₃, C₂H₅, OCH₃, CN, or combinations thereof.

32. A compound according to claim 1, wherein R⁴ is phenyl, naphthyl, biphenyl, furanyl, pyrazinyl, pyrimidinyl, pyridyl, quinolinyl, and isoquinolinyl, which in each case is unsubstituted or is substituted one or more times by OH, F, Cl, CF₃, methyl, ethyl, methoxy, ethoxy, CN, vinyl, CH₂OH, CONHOH, CONH₂, methylenedioxy, COOH, or combinations thereof.

33. A compound according to claim 1, wherein R⁴ is phenyl which is unsubstituted or is substituted one or more times by OH, F, Cl, CF₃, methyl, ethyl, methoxy, ethoxy, CN, vinyl, CH₂OH, CONHOH, CONH₂, methylenedioxy, COOH, or combinations thereof.

34. A compound according to claim 1, wherein R³ is pyridylmethyl.

35. A compound according to claim 33, wherein R³ is pyridylmethyl.

36. A composition according to claim 16, further comprising another pharmaceutical agent selected from other PDE4 inhibitors, calcium channel blockers, cholinergic drugs, adenosine receptor modulators, ampakines, NMDA-R modulators, mGluR modulators, and cholinesterase inhibitors.

37. A method according to claim 24, wherein said patient is suffering from inflammation due to asthma, chronic bronchitis, chronic obstructive pulmonary disease, atopic dermatitis, urticaria, allergic rhinitis, allergic conjunctivitis, vernal conjunctivitis, esoniophilic granuloma, psoriasis, inflammatory arthritis, rheumatoid arthritis, septic shock, ulcerative colitis, Crohn's disease, reperfusion injury of the myocardium, reperfusion injury of the brain, chronic glomerulonephritis, endotoxic shock, adult respiratory distress syndrome, cystic fibrosis, arterial restenosis, artherosclerosis, keratosis, rheumatoid spondylitis, osteoarthritis, pyresis, diabetes mellitus, pneumoconiosis, chronic obstructive airways disease, toxic contact eczema, allergic contact eczema, atopic eczema, seborrheic eczema, lichen simplex, sunburn, pruritis in the anogenital area, alopecia areata, hypertrophic scars, discoid lupus erythematosus, systemic lupus erythematosus, follicular pyodermias, wide-area pyodermias, endogenous acne, exogenous acne, acne rosacea, Behcet's disease, anaphylactoid purpura nephritis, inflammatory bowel disease, leukemia, multiple sclerosis, gastrointestinal disease, or autoimmune disease.

38. A method for enhancing cognition by decreasing phosphodiesterase 4 levels in a patient comprising administering to said patient an effective amount of a compound according to claim 1.

39. A method according to claim 37, wherein said patient is suffering from inflammation due to asthma.

40. A method according to claim 37, wherein said patient is suffering from inflammation due to chronic obstructive pulmonary disease.

* * * * *

UNITED STATES PATENT AND TRADEMARK OFFICE
CERTIFICATE OF CORRECTION

PATENT NO. : 7,153,871 B2
APPLICATION NO. : 10/622117
DATED : December 26, 2006
INVENTOR(S) : Allen T. Hopper It is certified that error appears in the above-identified patent and that said Letters Patent is hereby corrected as shown below:

Column 27, line 55, reads "and the ailcyl" should read -- and the alkyl --
Column 28, line 27, reads "aminoalkoxy" should read -- aminoalkoxy, --
Column 28, line 45, reads "thereof" should read -- thereof, --
Column 28, line 59, reads "aminoalkoxy" should read -- aminoalkoxy, --
Column 29, line 11, reads "noalkoxy" should read -- noalkoxy, --
Column 29, line 19, reads "N, 0 or S" should read -- N, O or S --
Column 29, line 20, delete "which"
Column 29, line 64, reads "0 or S;" should read -- O or S; --
Column 30, line 50, reads "may be partially" should read -- may be aromatic, or partially --
Column 30, line 66, reads "noalkoxy" should read -- noalkoxy, --
Column 31, line 9, reads "aminoalkoxy" should read -- aminoalkoxy, --
Column 31, line 53, reads "aminoalkoxy" should read -- aminoalkoxy, --
Column 32, line 22, reads "aminoalkoxy" should read -- aminoalkoxy, --
Column 32, line 47, reads "...N-(3pyridylmethyl]..." should read -- ...N-(3-pyridylmethyl)]... --
Column 33, line 14, reads "...N-(3-pyridylmethyl]..." should read -- ...N-(3-pyridylmethyl)... --
Column 33, line 60, reads "$R^5$-$SO_2$-NH-alkylene-O-," should read -- $R^5$-$SO_2$-NH-, $R^5$-$SO_2$-NH-alkylene-O-, --
Column 34, line 17, reads "COCH3" should read -- $COCH_3$ --
Column 34, line 43, reads "$R^9$is" should read -- $R^9$ is --
Column 34, line 59, reads "$R^9$is" should read -- $R^9$ is --
Column 35, line 28, delete "are"
Column 35, line 30, delete "are"
Column 35, line 31, delete "are"
Column 35, line 33, delete "are"
Column 35, line 35, delete "are"
Column 35, line 37, delete "are"
Column 35, line 39, delete "are"

UNITED STATES PATENT AND TRADEMARK OFFICE
CERTIFICATE OF CORRECTION

PATENT NO.       : 7,153,871 B2
APPLICATION NO.  : 10/622117
DATED            : December 26, 2006
INVENTOR(S)      : Allen T. Hopper It is certified that error appears in the above-identified patent and that said Letters Patent is hereby corrected as shown below:

Column 35, line 41, delete "are"

Signed and Sealed this

Seventeenth Day of November, 2009

David J. Kappos
*Director of the United States Patent and Trademark Office*